United States Patent [19]
Gold et al.

[11] Patent Number: 6,020,130
[45] Date of Patent: *Feb. 1, 2000

[54] NUCLEIC ACID LIGANDS THAT BIND TO AND INHIBIT DNA POLYMERASES

[75] Inventors: Larry Gold; Sumedha Jayasena, both of Boulder, Colo.

[73] Assignee: NeXstar Pharmaceuticals, Inc., Boulder, Colo.

[*] Notice: This patent is subject to a terminal disclaimer.

[21] Appl. No.: 08/945,734

[22] PCT Filed: Jun. 5, 1996

[86] PCT No.: PCT/US96/09451

§ 371 Date: Oct. 28, 1997

§ 102(e) Date: Oct. 28, 1997

[87] PCT Pub. No.: WO96/41010

PCT Pub. Date: Dec. 19, 1996

Related U.S. Application Data

[63] Continuation-in-part of application No. 08/487,426, Jun. 7, 1995, Pat. No. 5,763,173, application No. 08/487,720, Jun. 7, 1995, Pat. No. 5,874,557, and application No. 08/484,557, Jun. 7, 1995, Pat. No. 5,693,502.

[51] Int. Cl.[7] .............................. C12P 1/68; C12Q 19/34; C07H 21/02; C07H 21/04

[52] U.S. Cl. .......................... 435/6; 435/91.2; 435/194; 435/810; 536/22.1; 536/25.4; 536/24.3; 935/77; 935/78

[58] Field of Search .................... 435/6, 91.2, 194, 435/810; 536/22.1, 25.4, 24.3; 935/77, 78

[56] References Cited

U.S. PATENT DOCUMENTS

| | | | |
|---|---|---|---|
| 5,270,163 | 12/1993 | Gold et al. | 435/6 |
| 5,338,671 | 8/1994 | Scalice et al. | 435/91.2 |
| 5,459,015 | 10/1995 | Janjic et al. | 435/6 |
| 5,472,841 | 12/1995 | Jayasena et al. | 435/6 |
| 5,476,766 | 12/1995 | Gold et al. | 435/6 |
| 5,496,938 | 3/1996 | Gold et al. | 435/6 |
| 5,503,978 | 4/1996 | Schneider et al. | 435/6 |
| 5,527,894 | 6/1996 | Gold et al. | 435/6 |
| 5,543,293 | 8/1996 | Gold et al. | 435/6 |
| 5,567,588 | 10/1996 | Gold et al. | 435/6 |
| 5,580,737 | 12/1996 | Polisky et al. | 435/6 |
| 5,587,468 | 12/1996 | Allen et al. | 435/6 |
| 5,595,877 | 1/1997 | Gold et al. | 435/6 |
| 5,723,323 | 3/1998 | Kauffman et al. | 435/6 |

FOREIGN PATENT DOCUMENTS

| | | |
|---|---|---|
| 2 183 661 A | 6/1987 | United Kingdom . |
| WO 89/06694 | 7/1989 | WIPO . |
| WO 92/14843 | 9/1992 | WIPO ........................ 435/6 |
| WO 94/25037 | 11/1994 | WIPO . |

OTHER PUBLICATIONS

Oliphant et al. (1986) Gene 44:177.
Robertson & Joyce (1990) Nature 344:467.
Takase–Yoden et al. (1995) Antiviral Research 28:359.
Tamura et al. (1995) Nucleic Acids Research 34:93.
Thiesen & Bach (1990) Nucleic Acids Research 18:3203.
Tökm̈es and Aradi (1995) Biochimica et Biophysica Acta 1261:115.
Tuerk et al. (1992) Proc. Natl. Acad. Sci. USA 89:6988.
Ellington & Szostak (1990) Abstracts of papers presented at the 1990 meeting on RNA Processing, Cold Spring Harbor Laboratory, Cold Spring Harbor, NY, p. 84.
Fujihashi et al. (1995) AIDS Research and Human Retroviruses 11:461.
Hacia et al. (1994) 33:6192.
Joyce (1989) Gene 82:83.

(List continued on next page.)

Primary Examiner—Stephanie Zitomer
Attorney, Agent, or Firm—Swanson & Bratschun LLC

[57] ABSTRACT

This invention discloses high-affinity oligonucleotide ligands to the thermostable Taq polymerase and Tth polymerase. Specifically, this invention discloses DNA ligands having the ability to bind to the Taq and Tth polymerases and the methods for obtaining such ligands. The ligands are capable of inhibiting polymerases at ambient temperatures.

17 Claims, 17 Drawing Sheets

OTHER PUBLICATIONS

Joyce & Inoue (1989) Nucleic Acids Research 17:711.
Kellogg et al. (1994) BioTechniques 16:1134.
Kinzler & Vogelstein (1989) Nucleic Acids Research 17:3645.
Kramer et al. (1974) J. Mol. Biol. 89:719.
Levisohn & Spiegelman (1969) Proc. Natl. Acad. Sci. USA 63:805.
Levisohn & Spiegelman (1968) Proc. Natl. Acad. Sci. USA 60:866.
Matsukura et al. (1995) Toxicology Letters 82/83:435.
Meyers and Gelfand (1991) Biochemistry 30:7661.
Oliphant et al. (1989) Mol. Cell. Biol. 9:2944.
Oliphant & Struhl (1988) Nucleic Acids Research 16:7673.
Oliphant & Struhl (1987) Methods in Enzymology 155:568.
Tuerk et al., PNA, USA 89:6988–6992, Aug. 1992.
Boiziau et al. (1995) Nucleic Acids Research 23:64.
Bloch (1992) Applications, A Forum for PCR Users, Issue 8, pp. 6–9.
Chen and Gold (1994) Biochemistry 33:8746.

Polymerase Activity Assay

Polymerase
dNTPs
M$^{++}$

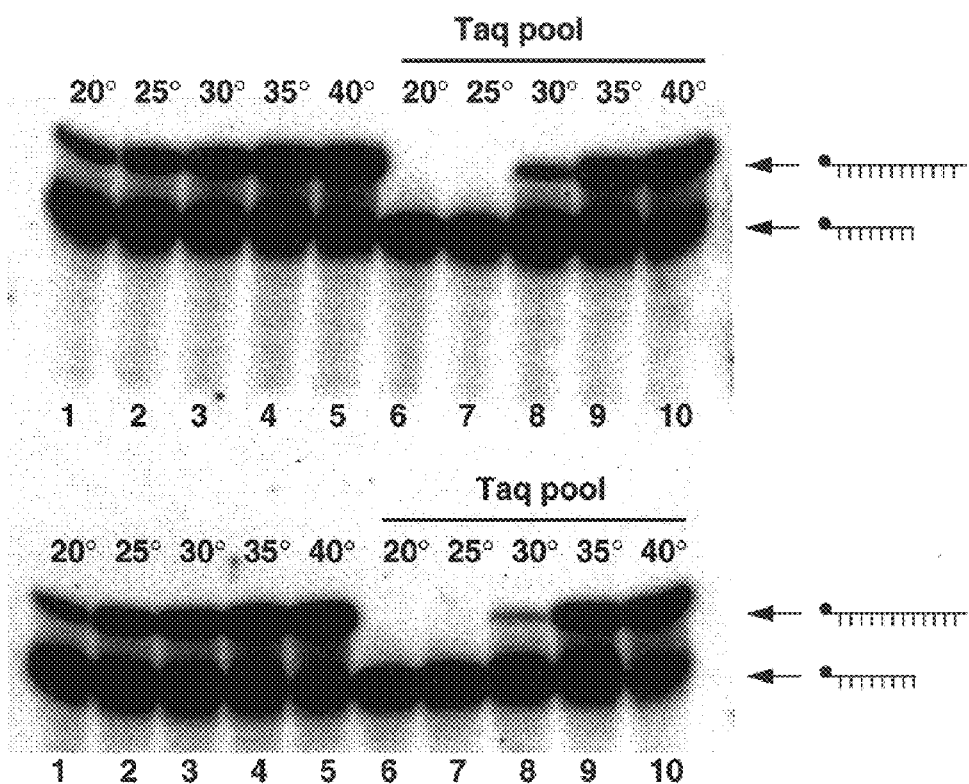

SEQUENCE LISTING (1) GENERAL INFORMATION:

(iii) NUMBER OF SEQUENCES: 73

(2) INFORMATION FOR SEQ ID NO:1:

(i) SEQUENCE CHARACTERISTICS:
      (A) LENGTH: 78 base pairs
      (B) TYPE: nucleic acid
      (C) STRANDEDNESS: single
      (D) TOPOLOGY: linear (ii) MOLECULE TYPE: DNA (ix) FEATURE:

(xi) SEQUENCE DESCRIPTION: SEQ ID NO:1:

TTCTCGGTTG GTCTCTGGCG GAGCNNNNNN NNNNNNNNNN NNNNNNNNNN    50

NNNNTCTTGT GTATGATTCG CTTTTCCC    78

(2) INFORMATION FOR SEQ ID NO:2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:2:

TTCTCGGTTG GTCTCTGGCG GAGC    24

(2) INFORMATION FOR SEQ ID NO:3:

(i) SEQUENCE CHARACTERISTICS:
      (A) LENGTH: 26 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:3:

TAGGGAAAAG CGAATCATAC ACAAGA    26

(2) INFORMATION FOR SEQ ID NO:4:

(i) SEQUENCE CHARACTERISTICS:
      (A) LENGTH: 33 base pairs
      (B) TYPE: nucleic acid
      (C) STRANDEDNESS: single (D) TOPOLOGY:  linear (xi) SEQUENCE DESCRIPTION:  SEQ ID NO:4:

GGCGAATTCT TCTCGGTTGG TCTCTGGCGG AGC                                33

(2) INFORMATION FOR SEQ ID NO:5:

(i) SEQUENCE CHARACTERISTICS:
            (A) LENGTH: 50 base pairs
            (B) TYPE:  nucleic acid
            (C) STRANDEDNESS:  single
            (D) TOPOLOGY:  linear (ii) MOLECULE TYPE:  DNA (xi) SEQUENCE DESCRIPTION:  SEQ ID NO:5:

CGCGGATCCT AATACGACTC ACTATAGGGA AAAGCGAATC ATACACAAGA              50

(2) INFORMATION FOR SEQ ID NO:6:

(i) SEQUENCE CHARACTERISTICS:
            (A) LENGTH:  49 base pairs
            (B) TYPE:  nucleic acid
            (C) STRANDEDNESS:  single
            (D) TOPOLOGY:  linear (ii) MOLECULE TYPE:  DNA (xi) SEQUENCE DESCRIPTION:  SEQ ID NO:6:

ATGCCTAAGT TTCGAACGCG GCTAGCCAGC TTTTGCTGGC TAGCCGCGT               49

(2) INFORMATION FOR SEQ ID NO:7:

(i) SEQUENCE CHARACTERISTICS:
            (A) LENGTH:  74 base pairs
            (B) TYPE:  nucleic acid
            (C) STRANDEDNESS:  single
            (D) TOPOLOGY:  linear (ii) MOLECULE TYPE:  DNA (xi) SEQUENCE DESCRIPTION:  SEQ ID NO:7:

TTCTCGGTTG GTCTCTGGCG GAGCTATCGT TTACTCATTG TTTTGTGTGT              50

TCTTGTGTAT GATTCGCTTT TCCC                                          74

(2) INFORMATION FOR SEQ ID NO:8:

(i) SEQUENCE CHARACTERISTICS:
            (A) LENGTH:  77 base pairs
            (B) TYPE:  nucleic acid
            (C) STRANDEDNESS:  single
            (D) TOPOLOGY:  linear (ii) MOLECULE TYPE:  DNA (xi) SEQUENCE DESCRIPTION:  SEQ ID NO:8:

TTCTCGGTTG GTCTCTGGCG GAGCACATTA CCCGAGACAT TCCTGACGTT              50

TTGTCTTGTG TATGATTCGC TTTTCCC                                       77

(2) INFORMATION FOR SEQ ID NO:9:

(i) SEQUENCE CHARACTERISTICS:
            (A) LENGTH:  72 base pairs
            (B) TYPE:  nucleic acid
            (C) STRANDEDNESS:  single
            (D) TOPOLOGY:  linear (ii) MOLECULE TYPE:  DNA (xi) SEQUENCE DESCRIPTION: SEQ ID NO:9:

```
TTCTCGGTTG GTCTCTGGCG GAGCTGCTGC TCCTTGTTCG TTTTGTCTTC        50

TTGTGTATGA TTCGCTTTTC CC                                      72
```

(2) INFORMATION FOR SEQ ID NO:10:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
TTCTCGGTTG GTCTCTGGCG GAGCAGCTTT TGGGGACATT CTAACGTTTT        50

GTCATCTTGT GTATGATTCG CTTTTCCC                                78
```

(2) INFORMATION FOR SEQ ID NO:11:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

```
TTCTCGGTTG GTCTCTGGCG GAGCAGATGC TTCAGTTTTC TCTCCGTGTC        50

TTGTGTATGA TTCGCTTTTC CC                                      72
```

(2) INFORMATION FOR SEQ ID NO:12:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
TTCTCGGTTG GTCTCTGGCG GAGCTCTTTT GGACTGAAGG TTTGTTGGTT        50

CTTGTGTATG ATTCGCTTTT CCC                                     73
```

(2) INFORMATION FOR SEQ ID NO:13:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
TTCTCGGTTG GTCTCTGGCG GAGCATGGTC TTTTTGTTGT TTGTTTGTCT        50

TGTGTATGAT TCGCTTTTCC C                                       71
```

(2) INFORMATION FOR SEQ ID NO:14:

(i) SEQUENCE CHARACTERISTICS:
        (A) LENGTH: 73 base pairs (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:14:

TTCTCGGTTG GTCTCTGGCG GAGCGTGACT TTTTACTTGT CCTAGGCTGT           50

CTTGTGTATG ATTCGCTTTT CCC                                        73

(2) INFORMATION FOR SEQ ID NO:15:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

TTCTCGGTTG GTCTCTGGCG GAGCCATCTA TGTCTTCTTT ATATTTGGTC           50

TTGTGTATGA TTCGCTTTTC CC                                         72

(2) INFORMATION FOR SEQ ID NO:16:

(i) SEQUENCE CHARACTERISTICS:
            (A) LENGTH: 72 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

TTCTCGGTTG GTCTCTGGCG GAGCACTACC TGGTTGTGTG CTTTCCATTC           50

TTGTGTATGA TTCGCTTTTC CC                                         72

(2) INFORMATION FOR SEQ ID NO:17:

(i) SEQUENCE CHARACTERISTICS:
            (A) LENGTH: 78 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:17:

TTCTCGGTTG GTCTCTGGCG GAGCATCCAT GAGACTAGGT TGGTTAGGGT           50

GGTGTCTTGT GTATGATTCG CTTTTCCC                                   78

(2) INFORMATION FOR SEQ ID NO:18:

(i) SEQUENCE CHARACTERISTICS:
            (A) LENGTH: 78 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

TTCTCGGTTG GTCTCTGGCG GAGCCCCTCA TAGTTTAACT TTACCTGGCT           50

TATCTCTTGT GTATGATTCG CTTTTCCC                                   78

(2) INFORMATION FOR SEQ ID NO:19:

(i) SEQUENCE CHARACTERISTICS:
        (A) LENGTH:  74 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:19:

```
TTCTCGGTTG GTCTCTGGCG GAGCAGTGAA CACCTTCTGT TTCGTGAGTC          50

TCTTGTGTAT GATTCGCTTT TCCC                                      74
```

(2) INFORMATION FOR SEQ ID NO:20:

(i) SEQUENCE CHARACTERISTICS:
        (A) LENGTH:  71 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:20:

```
TTCTCGGTTG GTCTCTGGCG GAGCCGTGTG TCTTAGTTAG CTCGTGGTCT          50

TGTGTATGAT TCGCTTTTCC C                                         71
```

(2) INFORMATION FOR SEQ ID NO:21:

(i) SEQUENCE CHARACTERISTICS:
        (A) LENGTH:  70 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:21:

```
TTCTCGGTTG GTCTCTGGCG GAGCTAACGT TGTGTGTTCT GTGCTATCTT          50

GTGTATGATT CGCTTTTCCC                                           70
```

(2) INFORMATION FOR SEQ ID NO:22:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:22:

```
TTCTCGGTTG GTCTCTGGCG GAGCAACAGA TTTGGTCATA TTCCTTGGTC          50

TTGTGTATGA TTCGCTTTTC CC                                        72
```

(2) INFORMATION FOR SEQ ID NO:23:

(i) SEQUENCE CHARACTERISTICS:
        (A) LENGTH:  76 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:23:

```
TTCTCGGTTG GTCTCTGGCG GAGCTGTGTT ATGCTCCGGT AACAATGCCC        50

TTTCTTGTGT ATGATTCGCT TTTCCC                                  76

(2) INFORMATION FOR SEQ ID NO:24:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

TTCTCGGTTG GTCTCTGGCG GAGCAATTGT AATTTCGGTA TCTCTGTCTT        50

GTGTATGATT CGCTTTTCCC                                         70

(2) INFORMATION FOR SEQ ID NO:25:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

TTCTCGGTTG GTCTCTGGCG GAGCGCAATT TCCTGTCCAA TCATTGTAGT        50

CTTGTGTATG ATTCGCTTTT CCC                                     73

(2) INFORMATION FOR SEQ ID NO:26:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

TTCTCGGTTG GTCTCTGGCG GAGCGCTTGA AGCTTTCACC CATCCTRATC        50

TTGTGTATGA TTCGCTTTTC CC                                      72

(2) INFORMATION FOR SEQ ID NO:27:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

TTCTCGGTTG GTCTCTGGCG GAGCCTTCTC CTTTATATGT CTTACCATCT        50

TGTGTATGAT TCGCTTTTCC C                                       71

(2) INFORMATION FOR SEQ ID NO:28:

(i) SEQUENCE CHARACTERISTICS:
        (A) LENGTH: 73 base pairs
        (B) TYPE: nucleic acid
        (C) STRANDEDNESS: single
```

```
        (D) TOPOLOGY: linear (ii) MOLECULE TYPE: DNA (xi) SEQUENCE DESCRIPTION: SEQ ID NO:28:

TTCTCGGTTG GTCTCTGGCG GAGCTATCGA GTAGACCCTG TTGTTCGTGT        50

CTTGTGTATG ATTCGCTTTT CCC                                    73

(2) INFORMATION FOR SEQ ID NO:29:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

TTCTCGGTTG GTCTCTGGCG GAGCCGCGTC TAGCTAAGAT TTCTACTGAT        50

GCATTCTTGT GTATGATTCG CTTTTCCC                               78

(2) INFORMATION FOR SEQ ID NO:30:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TTCTCGGTTG GTCTCTGGCG GAGCATGATT TTATGTTTAT CCTGTTTTCT        50

TGTGTATGAT TCGCTTTTCC C                                      71

(2) INFORMATION FOR SEQ ID NO:31:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

TTCTCGGTTG GTCTCTGGCG GAGCCAGTCG CTGTACGTGC TCTCCCTATG        50

TAACTCTTGT GTATGATTCG CTTTTCCC                               78

(2) INFORMATION FOR SEQ ID NO:32:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TTCTCGGTTG GTCTCTGGCG GAGCCAATCG GTGTACAATA TCTTCCTCTT        50

GTGTATGATT CGCTTTTCCC                                        70

(2) INFORMATION FOR SEQ ID NO:33:
```

```
    (i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:33:

TTCTCGGTTG GTCTCTGGCG GAGCCGTTAG CTGGTTAGTT AGTACTAGTC          50

TTGTGTATGA TTCGCTTTTC CC                                       72

(2) INFORMATION FOR SEQ ID NO:34:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:34:

TTCTCGGTTG GTCTCTGGCG GAGCAGGTAA GCGATTATGG GGTTATCGTC          50

TTGTGTATGA TTCGCTTTTC CC                                       72

(2) INFORMATION FOR SEQ ID NO:35:

(i) SEQUENCE CHARACTERISTICS:
        (A) LENGTH:  72 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:35:

TTCTCGGTTG GTCTCTGGCG GAGCTAGTTA CATGAACTAA TCGTGGAGTC          50

TTGTGTATGA TTCGCTTTTC CC                                       72

(2) INFORMATION FOR SEQ ID NO:36:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:36:

TTCTCGGTTG GTCTCTGGCG GAGCTCAATA CACAAATTGA TGTACAGTGT          50

CGATTCTTGT GTATGATTCG CTTTTCCC                                 78

(2) INFORMATION FOR SEQ ID NO:37:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:37:

TTCTCGGTTG GTCTCTGGCG GAGCCAAGCG GAAACAATGT ACAGTATTGG          50
```

GATCTCTTGT GTATGATTCG CTTTTCCC                    78

(2) INFORMATION FOR SEQ ID NO:38:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

TTCTCGGTTG GTCTCTGGCG GAGCGATGTA CAGTATCGCT ATCGAAAGAG        50

GCTGTCTTGT GTATGATTCG CTTTTCCC                    78

(2) INFORMATION FOR SEQ ID NO:39:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

TTCTCGGTTG GTCTCTGGCG GAGCGATGTA CAGTATCGCT ATCGAAAGAG        50

GCTGTCTTGT GTATGATTCG CTTTTCCC                    78

(2) INFORMATION FOR SEQ ID NO:40:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

TTCTCGGTTG GTCTCTGGCG GAGCGATGTA CAGTATCGCT ATCGAAAGAG        50

GCTGTCTTGT GTATGATTCG CTTTTCCC                    78

(2) INFORMATION FOR SEQ ID NO:41:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

TTCTCGGTTG GTCTCTGGCG GAGCGATGTA CAGTATCGCT ATCGAAAGAG        50

GCTGTCTTGT GTATGATTCG CTTTTCCC                    78

(2) INFORMATION FOR SEQ ID NO:42:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE:  DNA (xi) SEQUENCE DESCRIPTION:  SEQ ID NO:42:

TTCTCGGTTG GTCTCTGGCG GAGCAAGGCC ATTGATGTAC AGTATCAATG          50

CTGCTCTTGT GTATGATTCG CTTTTCCC                                 78

(2) INFORMATION FOR SEQ ID NO:43:

(i) SEQUENCE CHARACTERISTICS:
        (A) LENGTH:  76 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:43:

TTCTCGGTTG GTCTCTGGCG GAGCAAGTGT ACAGTAGTTG CCTACGCTAG          50

TGTCTTGTGT ATGATTCGCT TTTCCC                                   76

(2) INFORMATION FOR SEQ ID NO:44:

(i) SEQUENCE CHARACTERISTICS:
        (A) LENGTH:  76 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:44:

TTCTCGGTTG GTCTCTGGCG GAGCAAGTGT ACAGTAGTTG CCTACGCTAG          50

TGTCTTGTGT ATGATTCGCT TTTCCC                                   76

(2) INFORMATION FOR SEQ ID NO:45:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:45:

TTCTCGGTTG GTCTCTGGCG GAGCAATGTG CAGTATTGAT ATCGCTGGTG          50

GTCATCTTGT GTATGATTCG CTTTTCCC                                 78

(2) INFORMATION FOR SEQ ID NO:46:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:46:

TTCTCGGTTG GTCTCTGGCG GAGCACAATG TGAAGTATTG GGGTACGTCA          50

GTAGTCTTGT GTATGATTCG CTTTTCCC                                 78

(2) INFORMATION FOR SEQ ID NO:47:

(i) SEQUENCE CHARACTERISTICS:

(A) LENGTH:  78 base pairs
           (B) TYPE:  nucleic acid
           (C) STRANDEDNESS:  single
           (D) TOPOLOGY:  linear (ii) MOLECULE TYPE:  DNA (xi) SEQUENCE DESCRIPTION:  SEQ ID NO:47:

TTCTCGGTTG GTCTCTGGCG GAGCAATTGG GAAACAATGT GCAGTATGTG           50

AAGGTCTTGT GTATGATTCG CTTTTCCC                                  78

(2) INFORMATION FOR SEQ ID NO:48:

(i) SEQUENCE CHARACTERISTICS:
           (A) LENGTH:  78 base pairs
           (B) TYPE:  nucleic acid
           (C) STRANDEDNESS:  single
           (D) TOPOLOGY:  linear (ii) MOLECULE TYPE:  DNA (xi) SEQUENCE DESCRIPTION:  SEQ ID NO:48:

TTCTCGGTTG GTCTCTGGCG GAGCAAGTGT GCAGTAGTTA CTCATAAGAG           50

ACCATCTTGT GTATGATTCG CTTTTCCC                                  78

(2) INFORMATION FOR SEQ ID NO:49:

(i) SEQUENCE CHARACTERISTICS:
           (A) LENGTH:  78 base pairs
           (B) TYPE:  nucleic acid
           (C) STRANDEDNESS:  single
           (D) TOPOLOGY:  linear (ii) MOLECULE TYPE:  DNA (xi) SEQUENCE DESCRIPTION:  SEQ ID NO:49:

TTCTCGGTTG GTCTCTGGCG GAGCAGTGTG CAGTAGTGTG ATGTCAGAGT           50

ATCCTCTTGT GTATGATTCG CTTTTCCC                                  78

(2) INFORMATION FOR SEQ ID NO:50:

(i) SEQUENCE CHARACTERISTICS:
           (A) LENGTH:  78 base pairs
           (B) TYPE:  nucleic acid
           (C) STRANDEDNESS:  single
           (D) TOPOLOGY:  linear (ii) MOLECULE TYPE:  DNA (xi) SEQUENCE DESCRIPTION:  SEQ ID NO:50:

TTCTCGGTTG GTCTCTGGCG GAGCAGTGTG CGGTAGTGTG ATCTGAGAGT           50

ATCCTCTTGT GTATGATTCG CTTTTCCC                                  78

(2) INFORMATION FOR SEQ ID NO:51:

(i) SEQUENCE CHARACTERISTICS:
           (A) LENGTH:  77 base pairs
           (B) TYPE:  nucleic acid
           (C) STRANDEDNESS:  single
           (D) TOPOLOGY:  linear (ii) MOLECULE TYPE:  DNA (xi) SEQUENCE DESCRIPTION:  SEQ ID NO:51:

TTCTCGGTTG GTCTCTGGCG GAGCAGTGTG TAGTAGTGTT ACGATGGGGA           50

CGGTCTTGTG TATGATTCGC TTTTCCC                                   77

(2) INFORMATION FOR SEQ ID NO:52:

(i) SEQUENCE CHARACTERISTICS:
        (A) LENGTH:  76 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:52:

```
TTCTCGGTTG GTCTCTGGCG GAGCAAGTGT ACAGTAGTTG CCTACGCTAG          50

TGTCTTGTGT ATGATTCGCT TTTCCC                                   76
```

(2) INFORMATION FOR SEQ ID NO:53:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:53:

```
TTCTCGGTTG GTCTCTGGCG GAGCAGTGTA CAGTAGTGTT CCCGGTAGAG          50

CTATTCTTGT GTATGATTCG CTTTTCCC                                 78
```

(2) INFORMATION FOR SEQ ID NO:54:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:54:

```
TTCTCGGTTG GTCTCTGGCG GAGCAAATGG GAAACAATGT GCAGTATTGG          50

AAGGTCTTGT GTATGATTCG CTTTTCCC                                 78
```

(2) INFORMATION FOR SEQ ID NO:55:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:55:

```
TTCTCGGTTG GTCTCTGGCG GAGCAAGACC AGACAATGTA CAGTATTGGC          50

CTGATCTTGT GTATGATTCG CTTTTCCC                                 78
```

(2) INFORMATION FOR SEQ ID NO:56:

(i) SEQUENCE CHARACTERISTICS:
        (A) LENGTH:  79 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION: SEQ ID NO:56:

TTCTCGGTTG GTCTCTGGCG GAGCAGGTGG GACATTCTTT GCGTTATGTC            50

TCTGATCTTG TGTATGATTC GCTTTTCCC                                  79

(2) INFORMATION FOR SEQ ID NO:57:

(i) SEQUENCE CHARACTERISTICS:
             (A) LENGTH:  77 base pairs
             (B) TYPE:  nucleic acid
             (C) STRANDEDNESS:  single
             (D) TOPOLOGY:  linear (ii) MOLECULE TYPE:  DNA (xi) SEQUENCE DESCRIPTION: SEQ ID NO:57:

TTCTCGGTTG GTCTCTGGCG GAGCAGGAAT CTGGGGCATT CTTTGCGTTT            50

GCGTCTTGTG TATGATTCGC TTTTCCC                                    77

(2) INFORMATION FOR SEQ ID NO:58:

(i) SEQUENCE CHARACTERISTICS:
             (A) LENGTH:  78 base pairs
             (B) TYPE:  nucleic acid
             (C) STRANDEDNESS:  single
             (D) TOPOLOGY:  linear (ii) MOLECULE TYPE:  DNA (xi) SEQUENCE DESCRIPTION: SEQ ID NO:58:

TTCTCGGTTG GTCTCTGGCG GAGCGATCAT CTCAGAGCAT TCTTAGCGTT            50

TTGTTCTTGT GTATGATTCG CTTTTCCC                                   78

(2) INFORMATION FOR SEQ ID NO:59:

(i) SEQUENCE CHARACTERISTICS:
             (A) LENGTH:  78 base pairs
             (B) TYPE:  nucleic acid
             (C) STRANDEDNESS:  single
             (D) TOPOLOGY:  linear (ii) MOLECULE TYPE:  DNA (xi) SEQUENCE DESCRIPTION: SEQ ID NO:59:

TTCTCGGTTG GTCTCTGGCG GAGCGAGAAC TCCGTTCTTA GCGTATTGGA            50

GTCCTCTTGT GTATGATTCG CTTTTCCC                                   78

(2) INFORMATION FOR SEQ ID NO:60:

(i) SEQUENCE CHARACTERISTICS:
             (A) LENGTH:  78 base pairs
             (B) TYPE:  nucleic acid
             (C) STRANDEDNESS:  single
             (D) TOPOLOGY:  linear (ii) MOLECULE TYPE:  DNA (xi) SEQUENCE DESCRIPTION: SEQ ID NO:60:

TTCTCGGTTG GTCTCTGGCG GAGCGATCAT CTAAGAGCAT TCTTAGCGTT            50

TTGGTCTTGT GTATGATTCG CTTTTCCC                                   78

(2) INFORMATION FOR SEQ ID NO:61:

(i) SEQUENCE CHARACTERISTICS:
             (A) LENGTH:  78 base pairs
             (B) TYPE:  nucleic acid

```
        (C) STRANDEDNESS:  single
        (D) TOPOLOGY:  linear (ii) MOLECULE TYPE:  DNA (xi) SEQUENCE DESCRIPTION:  SEQ ID NO:61:

TTCTCGGTTG GTCTCTGGCG GAGCGGGCTC GGAACATTCT TAGCGTTTTG           50

TTCCTCTTGT GTATGATTCG CTTTTCCC                                  78

(2) INFORMATION FOR SEQ ID NO:62:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:62:

TTCTCGGTTG GTCTCTGGCG GAGCCAAAAC GAGAGAGCTT TCTGTGCGTT           50

TAGCTCTTGT GTATGATTCG CTTTTCCC                                  78

(2) INFORMATION FOR SEQ ID NO:63:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:63:

TTCTCGGTTG GTCTCTGGCG GAGCAATTGA AGTGACTTTC TCTGCGTTTA           50

GTCGTCTTGT GTATGATTCG CTTTTCCC                                  78

(2) INFORMATION FOR SEQ ID NO:64:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:64:

TTCTCGGTTG GTCTCTGGCG GAGCAATCGA TTGTTGAACA TTCTGACGTT           50

TTGTTCTTGT GTATGATTCG CTTTTCCC                                  78

(2) INFORMATION FOR SEQ ID NO:65:

(i) SEQUENCE CHARACTERISTICS:
        (A) LENGTH:  78 base pairs
        (B) TYPE:  nucleic acid
        (C) STRANDEDNESS:  single
        (D) TOPOLOGY:  linear (ii) MOLECULE TYPE:  DNA (xi) SEQUENCE DESCRIPTION:  SEQ ID NO:65:

TTCTCGGTTG GTCTCTGGCG GAGCAATCGA TTGTTGAACA TTCTGACGTT           50

TTGTTCTTGT GTATGATTCG CTTTTCCC                                  78
```

(2) INFORMATION FOR SEQ ID NO:66:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:66:

```
TTCTCGGTTG GTCTCTGGCG GAGCAGAAGC ATACGAAGAC ATTCCAACGT           50

TTTGTCTTGT GTATGATTCG CTTTTCCC                                  78
```

(2) INFORMATION FOR SEQ ID NO:67:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:67:

```
TTCTCGGTTG GTCTCTGGCG GAGCAGAAGC ATACGAAGAC ATTCCAACGT           50

TTTGTCTTGT GTATGATTCG CTTTTCCC                                  78
```

(2) INFORMATION FOR SEQ ID NO:68:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:68:

```
TTCTCGGTTG GTCTCTGGCG GAGCCTCAGG ATAAGGTCAT TCTAACGTTA           50

TGATCTTGTG TATGATTCGC TTTTCCC                                   77
```

(2) INFORMATION FOR SEQ ID NO:69:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:69:

```
TTCTCGGTTG GTCTCTGGCG GAGCGACCAA GCGTCAAGAT ATTCAAACGT           50

TTTATCTTGT GTATGATTCG CTTTTCCC                                  78
```

(2) INFORMATION FOR SEQ ID NO:70:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:70:

```
TTCTCGGTTG GTCTCTGGCG GAGCAGAAGC ATACGAAGAC ATTCCAACGT         50

TTGGTCTTGT GTATGATTCG CTTTTCCC                                78

(2) INFORMATION FOR SEQ ID NO:71:

(i) SEQUENCE CHARACTERISTICS:
         (A) LENGTH:  77 base pairs
         (B) TYPE:  nucleic acid
         (C) STRANDEDNESS:  single
         (D) TOPOLOGY:  linear (ii) MOLECULE TYPE:  DNA (xi) SEQUENCE DESCRIPTION:  SEQ ID NO:71:

TTCTCGGTTG GTCTCTGGCG GAGCTACGCT GACAGGCCAC GTTTTGTCAT         50

GATTCTTGTG TATGATTCGC TTTTCCC                                 77

(2) INFORMATION FOR SEQ ID NO:72:

(i) SEQUENCE CHARACTERISTICS:
         (A) LENGTH:  78 base pairs
         (B) TYPE:  nucleic acid
         (C) STRANDEDNESS:  single
         (D) TOPOLOGY:  linear (ii) MOLECULE TYPE:  DNA (xi) SEQUENCE DESCRIPTION:  SEQ ID NO:72:

TTCTCGGTTG GTCTCTGGCG GAGCATAGGC AGGGGACATT GCAACCTTTT         50

GTCATCTTGT GTATGATTCG CTTTTCCC                                78

(2) INFORMATION FOR SEQ ID NO:73:

(i) SEQUENCE CHARACTERISTICS:
         (A) LENGTH:  78 base pairs
         (B) TYPE:  nucleic acid
         (C) STRANDEDNESS:  single
         (D) TOPOLOGY:  linear (ii) MOLECULE TYPE:  DNA (xi) SEQUENCE DESCRIPTION:  SEQ ID NO:73:

TTCTCGGTTG GTCTCTGGCG GAGCCATTGG GCCAGAGGAA CACAACCTCA         50

ACAGTCTTGT GTATGATTCG CTTTTCCC                                78
```

NUCLEIC ACID LIGANDS THAT BIND TO AND INHIBIT DNA POLYMERASES

RELATED APPLICATIONS

This application is a 371 of PCT application Ser. No. PCT/US96/09451, filed on Jun. 5, 1996, which is a continuation in part of U.S. patent application Ser. No. 08/487,426, filed on Jun. 7, 1995, now U.S. Pat. No. 5,763,173, U.S. application Ser. No. 08/487,720, filed on Jun. 7, 1995, now U.S. Pat. No. 5,874,557, and U.S. patent application Ser. No. 08/484,557, filed on Jun. 7, 1995, now U.S. Pat. No. 5,693,502, each of which is entitled "Nucleic Acid Ligand Inhibitors to DNA Polymerases."

FIELD OF THE INVENTION

Described herein are methods for identifying and preparing high-affinity nucleic acid ligands to DNA polymerases, specifically thermostable DNA polymerases. In a preferred embodiment the DNA polymerase is selected from Taq polymerase, a thermostable polymerase isolated from *Thermus aquaticus* or Tth polymerase, a thermostable DNA polymerase and reverse transcriptase isolated from *Thermus thermophilus*. However, the method of this invention can be extended to the identification and preparation of any thermal stable DNA polymerase. The method utilized herein for identifying such nucleic acid ligands is called SELEX, an acronym for Systematic Evolution of Ligands by EXponential Enrichment. Also described herein is an improved method for performing the Polymerase Chain Reaction using the nucleic acid ligands of this invention. Specifically disclosed herein are high-affinity nucleic acid ligands to Taq polymerase and Tth polymerase. The invention includes high-affinity DNA ligands which bind to Taq polymerase and Tth polymerase, thereby inhibiting their ability to polymerase DNA synthesis at ambient temperatures. Further included within this invention are nucleic acid switches. The thermal dependent binding of the nucleic acid ligands to DNA polymerases of this invention are examples of ligands whose desirable properties can be switched on or off based on any number of reaction conditions.

BACKGROUND OF THE INVENTION

The Polymerase Chain Reaction (PCR), is a recently developed technique which has had a significant impact in many areas of science. PCR is a rapid and simple method for specifically amplifying a target DNA sequence in an exponential manner. (Saiki et al. (1985) Science 230:1350; Mullis and Faloona (1987) Methods Enzymol. 155:335). Briefly, the method consists of synthesizing a set of primers that have nucleotide sequences complementary to the DNA that flanks the target sequence. The primers are then mixed with a solution of the target DNA, a thermostable DNA polymerase and all four deoxynucleotides (A, T, C and G). The solution is then heated to a temperature sufficient to separate the complementary strands of DNA (approximately 95° C.) and then cooled to a temperature sufficient to allow the primers to bind to the flanking sequences. The reaction mixture is then heated again (to approximately 72° C.) to allow the DNA synthesis to proceed. After a short period of time the temperature of the reaction mixture is once again raised to a temperature sufficient to separate the newly formed double-stranded DNA, thus completing the first cycle of PCR. The reaction mixture is then cooled and the cycle is repeated. Thus, PCR consists of repetitive cycles of DNA melting, annealing and synthesis. Twenty replication cycles can yield up to a million fold amplification of the target DNA sequence. The ability to amplify a single DNA molecule by PCR has applications in environmental and food microbiology (Wernars et al. (1991) Appl. Env. Microbiol. 57:1914–1919; Hill and Keasler (1991) Int. J. Food Microbiol. 12:67–75), clinical microbiology (Wages et al. (1991) J. Med. Virol. 33:58–63; Sacramento et al. (1991) Mol. Cell Probes 5:229–240; Laure et al. (1988) Lancet 2:538), oncology (Kumar and Barbacid (1988) Oncogene 3:647–651; McCormick (1989) Cancer Cells 1:56–61; Crescenzi et al. (1988) Proc. Natl. Acad. Sci. USA 85:4869), genetic disease prognosis (Handyside et al. (1990) Nature 344:768–770), blood banking (Jackson (1990) Transfusion 30:51–57) and forensics (Higuchi et al. (1988) Nature (London) 332:543).

The availability of thermostable DNA polymerases such as Taq DNA polymerase has both simplified and improved PCR. Originally only heat-sensitive polymerases, such as *E. coli* DNA polymerase were available for use in PCR. Heat-sensitive polymerases, however, are destroyed at the temperatures required to melt double-stranded DNA, and additional polymerase has to be added after each PCR cycle. Taq DNA polymerase, isolated from the thermophilic bacterium *Thermus aquaticus*, is stable up to 95° C. and its use in PCR has eliminated the necessity of repetitive addition of temperature sensitive polymerases after each thermal cycle. Additionally, because Taq polymerase can be used at higher temperatures it has improved the specificity and sensitivity of PCR. The reason for the improved specificity is that at higher temperatures the binding of promoters to sites other that the desired ones (referred to as mispriming) is significantly reduced.

Since its discovery, the Polymerase Chain Reaction has been modified for various applications, such as in situ PCR, in which the detection limit of traditional in situ hybridization has been pushed to the single copy level (Haase et al. (1990) Proc. Natl. Acad. Sci. USA 87:4971–4975), and reverse transcriptase PCR (RT-PCR), wherein an RNA sequence is converted to its copy DNA (cDNA) by reverse transcriptase (RT) before being amplified by PCR, making RNA a substrate for PCR (Kawasaki (1991) Amplification of RNA in *PCR Protocols, A Guide to Methods and Applications*, Innis et al., Eds. Academic Press Inc., San Diego, Calif., 21–27). Mesophilic viral reverse transcriptases, however, are often unable to-synthesize full-length cDNA molecules because they cannot "read through" stable secondary structures of RNA molecules. This limitation has recently been overcome by use of a polymerase isolated from *Thermus thermophilus* (Tth polymerase). Tth polymerase is a thermostable polymerase that can function as both reverse transcriptase and DNA polymerase (Myers and Gelfand (1991) Biochemistry 30:7662–7666). The reverse transcription performed at an elevated temperature using Tth polymerase eliminates secondary structures of template RNA, making it possible for the synthesis of full-length cDNA.

Although significant progress has been made in PCR technology, the amplification of nontarget oligonucleotides due to side-reactions, such as mispriming of background DNA and/or primer oligomerization still presents a significant problem. This is especially true in diagnostic applications in which PCR is carried out in a milieu containing background DNA while the target DNA may be present in a single copy (Chou et al. (1992) Nucleic Acid Res. 20:1717–1723). It has been determined that these side reactions often occur when all reactants have been mixed at ambient temperature before thermal cycling is initiated.

Two methods have been reported which minimize these side reactions. In the first method, termed "hot start" PCR (Chou et al. (1992) Nucleic Acid Res. 20:1717–1723; D'Aquila et al. (1991) Nucleic Acid Res. 19:3749), all of the reagents are heated to 72° C. before adding the final reagent, usually the polymerase. In wax-mediated "hot start" PCR, a component(s) crucial to polymerase activity is physically separated from the rest of the reaction mixture at low temperature by a wax layer which melts upon heating in the first cycle (Chou et al. (1992) Nucleic Acids Res. 20:1717; Horton et al. (1994) BioTechniques 16:42). "Hot start" PCR has certain drawbacks; the requirement of reopening of tubes before initiating thermocycling increases crossover contamination and repetitive pipetting makes it tedious in handling a large number of samples. A reagent that could be placed directly in the reaction mixture with all other reaction components and inhibit the polymerase at ambient temperature would be useful to overcome limitations associated with "hot start" PCR. Although this method does increase specificity, thereby reducing side products, the method is inconvenient for dealing with a large number of samples, the reaction mixture can become more easily contaminated, and the method is error-prone.

In the second method, a neutralizing antibody to Taq polymerase (referred to as TaqStart) is added to the complete reaction mixture. This antibody inhibits the polymerase activity at ambient temperature (Kellogg et al. (1994) BioTechniques 16:1134–1137), but is inactivated by heat denaturation once the reaction is thermocycled, rendering the polymerase active. The drawback of this approach to reducing side products is that the anti-Taq antibody should be stored at −20° C. until use, which means that detection kits should be packaged and shipped under controlled environment adding to their cost. In addition, a significant amount of antibody (~1 µg of antibody/5 U of Taq polymerase) is needed for a single PCR.

The development of high affinity nucleic acid ligands capable of inhibiting the thermostable Taq and Tth polymerases would obviate the need for the "hot start" method and would overcome the limitations associated with the second method. Nucleic acid inhibitors can be developed that are extremely specific and have high affinity. Since nucleic acids are more stable than proteins at ambient temperature, the shipping and packaging problems associated with using antibodies can be overcome. Additionally, nucleic acids, like antibodies can be identified that will lose their affinity for the polymerase at higher temperatures, allowing the polymerase to be activated when desired. The potential for mispriming mediated by nucleic acid based inhibitors themselves functioning as primers (in addition to the specific primers used in the reaction) in PCR can be eliminated by capping their 3' ends.

X-ray crystal structures of several DNA polymerases have indicated that they fold into similar three dimensional structures. (For a review, see Joyce and Steitz (1994) Annu. Rev. Biochem. 63:777). The C-terminal domain responsible for polymerization is organized into three sub-domains representing "palm", "fingers", and "thumb", anatomically analogous to a right hand. Tth polymerase and Taq polymerase are 93% similar and 88% identical at the amino acid sequence level (Abramson (1995) in *PCR Strategies* (Academic Press, New York). Both are devoid of 3'→5' exonuclease activity, but contain 5'→3' exonuclease activity (Abramson (1995) in *PCR Strategies* (Academic Press, New York); Tindall and Kunkel (1988) Biochemistry 27:6008). Thus, nucleic acid ligand inhibitors might be expected to behave similarly toward both of these enzymes, as well as, other thermostable polymerases. This would make possible the use of a single inhibitor for a number of thermostable enzymes.

SELEX

A method for the in vitro evolution of nucleic acid molecules with highly specific binding to target molecules has been developed. This method, Systematic Evolution of Ligands by EXponential enrichment, termed SELEX, is described in U.S. patent application Ser. No. 07/536,428, entitled "Systematic Evolution of Ligands by Exponential Enrichment," now abandoned, U.S. patent application Ser. No. 07/714,131, filed Jun. 10, 1991, entitled "Nucleic Acid Ligands," now U.S. Pat. No. 5,475,096, U.S. patent application Ser. No. 07/931,473, filed Aug. 17, 1992, entitled "Methods for Identifying Nucleic Acid Ligands," now U.S. Pat. No. 5,270,163 (see also WO 91/19813, published Dec. 26, 1991), each of which is herein specifically incorporated by reference. Each of these applications, collectively referred to herein as the SELEX Patent Applications, describes a fundamentally novel method for making a nucleic acid ligand to any desired target molecule.

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity nucleic acid ligands to the target molecule.

The basic SELEX method has been modified to achieve a number of specific objectives. For example, U.S. patent application Ser. No. 07/960,093, filed Oct. 14, 1992, entitled "Method for Selecting Nucleic Acids on the Basis of Structure," now abandoned (See U.S. patent application Ser. No. 08/198,670, filed Feb. 22, 1994, entitled "Method for Selecting Nucleic Acids on the Basis of Structure," now U.S. Pat. No. 5,707,796), describes the use of SELEX in conjunction with gel electrophoresis to select nucleic acid molecules with specific structural characteristics, such as bent DNA. U.S. patent application Ser. No. 08/123,935, filed Sep. 17, 1993, entitled "Photoselection of Nucleic Acid Ligands" now abandoned (See U.S. patent application Ser. No. 08/612,895, filed Mar. 8, 1996, entitled "Systematic Evolution of Ligands by Exponential Enrichment: Photoselection of Nucleic Acid Ligands and Solution SELEX," now U.S. Pat. No. 5,736,177) describes a SELEX based method for selecting nucleic acid ligands containing photoreactive groups capable of binding and/or photocrosslinking to and/ or photoinactivating a target molecule. U.S. patent application Ser. No. 08/134,028, filed Oct. 7, 1993, entitled "High-Affinity Nucleic Acid Ligands That Discriminate Between Theophylline and Caffeine," abandoned in favor of U.S. patent application Ser. No. 08/443,957, filed May 18, 1995, entitled "High-Affinity Nucleic Acid Ligands That Discriminate Between Theophylline and Caffeine," now U.S. Pat. No. 5,580,737 describes a method for identifying highly specific nucleic acid ligands able to discriminate between closely related molecules, termed Counter-SELEX. U.S. patent application Ser. No. 08/143,564, filed Oct. 25, 1993, entitled "Systematic Evolution of Ligands by EXponential Enrichment: Solution SELEX," abandoned in favor of U.S. patent application Ser. No. 08/461,069, filed May 5, 1995, entitled "Systematic Evolution of Ligands by EXponential Enrichment: Solution SELEX," now U.S. Pat. No. 5,567,588 describes a SELEX-based method which achieves highly efficient partitioning between oligonucleotides having high and low affinity for a target molecule. U.S. patent application Ser. No. 07/964,624, filed Oct. 21, 1992, entitled "Nucleic Acid Ligands to HIV-RT and HIV-1 Rev," now U.S. Pat. No. 4,496,938, describes methods for obtaining improved nucleic acid ligands after SELEX has been performed. U.S. patent application Ser. No. 08/400,440, filed Mar. 8, 1995, entitled "Systematic Evolution of Ligands by EXponential Enrichment: Chemi-SELEX," now U.S. Pat. No. 5,705,337 describes methods for covalently linking a ligand to its target.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. patent application Ser. No. 08/117,991, filed Sep. 8, 1993, entitled "High Affinity Nucleic Acid Ligands Containing Modified Nucleotides," abandoned in favor of U.S. patent application Ser. No. 08/430,709, filed Apr. 27, 1995, entitled "High Affinity Nucleic Acid Ligands Containing Modified Nucleotides," now U.S. Pat. No. 5,660,985 that describes oligonucleotides containing nucleotide derivatives chemically modified at the 5- and 2'-positions of pyrimidines. U.S. patent application Ser. No. 08/134,028, supra, describes highly specific nucleic acid ligands containing one or more nucleotides modified with 2'-amino (2'-$NH_2$), 2'-fluoro (2'-F), and/or 2'-O-methyl (2'-OMe). U.S. patent application Ser. No. 08/264,029, filed Jun. 22, 1994, entitled "Novel Method of Preparation of Known and Novel Nucleosides by Intramolecular Nucleophilic Displacement," now abandoned describes oligonucleotides containing various 2'-modified pyrimidines.

The SELEX method encompasses combining selected oligonucleotides with other selected oligonucleotides and non-oligonucleotide functional units as described in U.S. patent application Ser. No. 08/284,063, filed Aug. 2, 1994, entitled "Systematic Evolution of Ligands by Exponential Enrichment: Chimeric SELEX," now U.S. Pat. No. 5,637,459 and U.S. patent application Ser. No. 08/234,997, filed Apr. 28, 1994, entitled "Systematic Evolution of Ligands by Exponential Enrichment: Blended SELEX," now U.S. Pat. No. 5,683,867, respectively. These applications allow the combination of the broad array of shapes and other properties, and the efficient amplification and replication properties, of oligonucleotides with the desirable properties of other molecules. Each of the above described patent applications which describe modifications of the basic SELEX procedure are specifically incorporated by reference herein in their entirety.

BRIEF SUMMARY OF THE INVENTION

The present invention includes methods of identifying and producing nucleic acid ligands to DNA polymerases. Specifically included are methods for identifying nucleic acid ligands to thermostable DNA polymerases useful in the Polymerase Chain Reaction, including the Taq and Tth polymerases and the nucleic acid ligands so identified and produced. More particularly, DNA sequences are provided that are capable of binding specifically to the Taq and Tth polymerases respectively, thereby inhibiting their ability to catalyze the synthesis of DNA at ambient temperatures. The method of this invention can be extended to identifying and producing nucleic acid ligands to any thermostable DNA polymerase and the ligands so identified and produced.

Further included in this invention is a method of identifying nucleic acid ligands and nucleic acid ligand sequences to the Taq and Tth polymerases comprising the steps of (a) preparing a candidate mixture of nucleic acids, (b) partitioning between members of said candidate mixture on the basis of affinity to the Taq or Tth polymerases and (c) amplifying the selected molecules to yield a mixture of nucleic acids enriched for nucleic acid sequences with a relatively higher affinity for binding to the Taq and Tth polymerases, respectively.

Further included in this invention is an improved method of performing the Polymerase Chain Reaction comprising the step of including a nucleic acid ligand that inhibits the thermostable polymerase at ambient temperatures, but dissociates from the polymerase at elevated temperatures. Such nucleic acid ligands are identified according to the method of this invention.

More specifically, the present invention includes the ssDNA ligands to Taq polymerase and Tth polymerase identified according to the above-described method, including those ligands listed in Tables 2–5 (SEQ ID NOS:7–74 and 76–77). Also included are DNA ligands to Taq polymerase and Tth polymerase that are substantially homologous to any of the given ligands and that have substantially the same ability to bind and inhibit the activity of Taq polymerase and Tth polymerase. Further included in this invention are DNA ligands to Taq polymerase and Tth polymerase that have substantially the same structural form as the ligands presented herein and that have substantially the same ability to bind and inhibit the activity of Taq polymerase and Tth polymerase.

The present invention also includes modified nucleotide sequences based on the DNA ligands identified herein and mixtures of the same.

The nucleic acid ligands of the present invention may function as "switches" in that they turn the Polymerase Chain Reaction "on" or "off" depending on the temperature of the reaction mixture. The present invention, therefore, also includes a method for identifying and preparing nucleic acid ligand sequences which function as switches comprising the steps of (a) preparing a candidate mixture of nucleic acids, (b) partitioning between members of said candidate mixture on the basis of affinity to the Taq or Tth polymerases and (c) amplifying the selected molecules using the target molecule to yield a mixture of nucleic acids enriched for nucleic acid sequences with a relatively higher affinity for binding to the Taq and Tth polymerases only at temperatures below the temperature of amplification, respectively.

The present invention, therefore, includes methods for identification of nucleic acid switches. Nucleic acids switches are nucleic acids identified by the SELEX process wherein the desired property of the nucleic acid can be "switched" on or off depending on the manipulation of some environmental parameter. Nucleic acid switches may be identified by manipulating the SELEX partitioning step to select for nucleic acids that give opposite results—often binding to the target—based on an alteration in a reaction medium parameter. The examples in this case demonstrate nucleic acid switches that are turned on and off based on temperature, however, the method of this invention can be extended to identifying and preparing nucleic ligands that function as switches on the basis of conditions other than temperature, including but not limited to, pH, concentration of specific ions, ie. $Mg^{++}$.

BRIEF DESCRIPTION OF THE FIGURES

FIGS. 5D and 5E illustrate a third polymerase activity assay for the Taq and Tth polymerases, resolved on a 15% polyacrylamide gel under denaturing conditions. FIG. 5D shows the activity of Taq polymerase in the presence of the enriched pool that has not been subjected to thermal cycling, whereas FIG. 5E exhibits the activity of Taq polymerase in the presence of the enriched pool that has been thermal cycled. Lanes 1–5 indicate the amount of product formed over 5 minute incubations at 20° C., 25° C., 30° C., 35° C. and 40° C., respectively. Lanes 6–10 exhibit Taq polymerase activity in the presence of the enriched pool over 5 minute incubations at 20° C., 25° C., 30° C., 35° C. and 40° C., respectively. The schematics on right depict the starting short end-labeled DNA and the polymerase extended product.

FIGS. 6C and 6D show the percent of product formed in the presence of ligand TQ21 (○) and ligand TQ30 (●) using Taq polymerase (FIG. 6C) and Tth polymerase (FIG. 6D), respectively. The amount of product was quantitated by phosphorimager and normalized to the product formed in the absence of an inhibitor at the same temperature to obtain the percent of product (FIGS. 6C and 6D (abscissa)).

FIG. 10A illustrates a comparison of amplification performed under standard conditions (lanes 1–3) with those of "hot start" PCR (lanes 4–6) in detecting the target at ~10 and 50 copies. FIG. 10B illustrates a comparison PCR amplifications conducted in the presence of a nonspecific (NS) oligonucleotide (lanes 1–3) with those of TQ21 (lanes 4–6) and TQ30 (lanes 7–9) in detecting the target at ~10 and 50 copies. FIG. 10C illustrates the detection of very low number target copies (as indicated) in the presence of oligonucleotide inhibitors TQ21 and TQ30. In both (B) and (C) oligonucleotide inhibitors were used at a concentration of 50 nM. M indicates molecular weight standards. Arrows in each panel shows the position of the target-specific 203-bp DNA in the gels.

FIG. 13A depicts a binding curve for ligand Trnc.21 to Taq polymerase. FIG. 13B illustrates the effect of Trnc.21 concentration on the activity of Taq polymerase (●) and Tth polymerase (○). $IC_{50}$ values for Taq polymerase and Tth polymerase are 21 and 36.5 nM, respectively. FIG. 13C depicts the effect of temperature on the inhibition of Taq polymerase (●) and Tth polymerase (○) by Trnc.21. The amount of product formed in the presence of the inhibitor at a given temperature was normalized to that formed in the absence of an inhibitor at the same temperature to obtain the percent product. The calculated $IT_{50}$ values for Taq polymerase and Tth polymerase are 34° C. and 35.6° C., respectively.

FIG. 14A depicts a binding curve for homodimer (D.30-D.30) to Taq polymerase ($K_d$=47.5±5 pM). FIG. 14B illustrates the effect of dimeric (●) and monomeric (○) ligand concentrations on the activity of Taq polymerase. The $IC_{50}$ value of Trnc.2-30 (monomer) is 48 nM, whereas that of D.30-D.30 (dimer) is 14 nM.

FIG. 15A illustrates the effect of D.21-D.30 concentration on the activity of Taq polymerase (●) and Tth polymerase (○). $IC_{50}$ values for the inhibition of these two polymerases are approximately 30 nM. FIG. 15B illustrates the effect of temperature on the inhibition of Taq polymerase (●) and Tth polymerase (○) by heterodimer D.21-D.30. The $IT_{50}$ value for Taq polymerase is 41° C., whereas that for Tth polymerase is 34.5° C.

FIG. 16A Nitrocellulose filter binding analysis of Trnc.21 in the presence of 1 mM dNTPs. Closed circles (●) indicate the binding in the absence of hairpin DNA template, whereas open circles (○) indicate the binding in the presence of 250 nM hairpin DNA template. The calculated $K_d$ values under these conditions are approximately 2.5 nM. FIG. 16B illustrates the effect of dNTP concentration on the binding of Trnc.21 to Taq polymerase. In this experiment binding of the radiolabeled Trnc.21 to 1 nM Taq polymerase was monitored in the presence of varying concentration of dNTPs.

DETAILED DESCRIPTION OF THE INVENTION

Figure 1A:
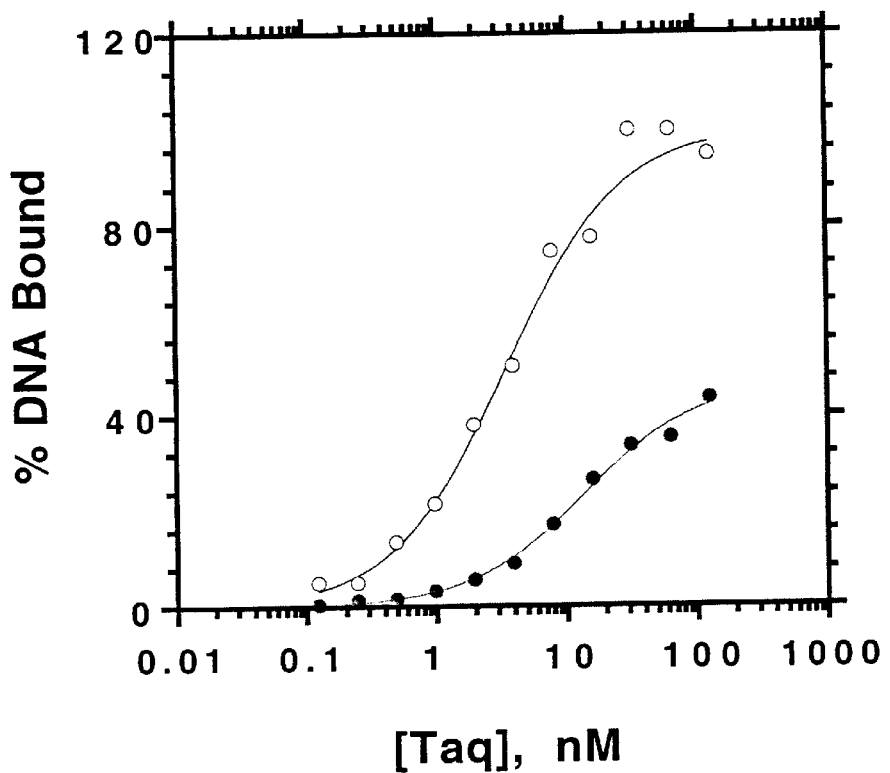
FIG. 1A shows the binding affinities of enriched pools of DNA after 12 rounds of SELEX (○) and the unselected random pool (●) of DNA for the Taq polymerase.

This application describes the isolation of nucleic acid ligands to DNA polymerases. Specifically, this application describes the isolation of nucleic acid ligands to thermostable polymerases useful in the Polymerase Chain Reaction. In a preferred embodiment the DNA polymerase is selected from Taq or Tth polymerase, however the method of this invention can be extended to the identification and purification of high-affinity nucleic acid ligands to any thermostable DNA polymerase. The nucleic acid ligands are identified through the method known as SELEX. SELEX is described in U.S. patent application Ser. No. 07/536,428, entitled Systematic Evolution of Ligands by EXponential Enrichment, now abandoned, U.S. patent application Ser. No. 07/714,131, filed Jun. 10, 1991, entitled Nucleic Acid Ligands, now U.S. Pat. No. 5,475,096 and U.S. patent application Ser. No. 07/931,473, filed Aug. 17, 1992, entitled Methods for Identifying Nucleic Acid Ligands, now U.S. Pat. No. 5,270,163, (see also WO 91/19813, published Dec. 26, 1991). These applications, each specifically incorporated herein by reference, are collectively called the SELEX Patent Applications.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5–50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for partitioning nucleic acids within a candidate mixture; and methods for amplifying partitioned nucleic acids to generate enriched candidate mixture. The SELEX Patent Applications also describe ligands obtained to a number of target species, including both protein targets where the protein is and is not a nucleic acid binding protein.

The SELEX process provides high affinity ligands of a target molecule. This represents a singular achievement that is unprecedented in the field of nucleic acids research. The present invention applies the SELEX procedure to the specific targets of nucleic acid inhibitors of DNA polymerases, particularly the Taq and Tth polymerases. In the Example section below, the experimental parameters used to isolate and identify the nucleic acid inhibitors to the Taq and Tth polymerases are described.

In co-pending and commonly assigned U.S. patent application Ser. No. 07/964,624, filed Oct. 21, 1992, now U.S. Pat. No. 5,496,938 ('938 patent), methods are described for obtaining improved nucleic acid ligands after SELEX has been performed. The '938 patent, entitled Nucleic Acid Ligands to HIV-RT and HIV-1 Rev, is specifically incorporated herein by reference.

Certain terms used to describe the invention herein are defined as follows:

"Nucleic Acid Ligand" as used herein is a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, facilitating the reaction between the target and another molecule. In the preferred embodiment, the action has specific binding affinity for a target molecule, such target molecule being a three dimensional chemical structure other than a polynucleotide that binds to the nucleic acid ligand through a mechanism which predominantly depends on Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target by the method comprising: a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids.

"Candidate Mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. In a preferred embodiment, each nucleic acid has fixed sequences surrounding a randomized region to facilitate the amplification process.

"Nucleic Acid" means either DNA, RNA, single-stranded or double-stranded and any chemical modifications thereof. Modifications include, but are not limited to, those which provide other chemical groups that incorporate additional charge, polarizability, hydrogen bonding, electrostatic interaction, and fluxionality to the nucleic acid ligand bases or to the nucleic acid ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, methylations, unusual base-pairing combinations such as the isobases isocytidine and isoguanidine and the like. Modifications can also include 3' and 5' modifications such as capping.

"SELEX" methodology involves the combination of selection of nucleic acid ligands which interact with a target in a desirable manner, for example binding to a protein, with amplification of those selected nucleic acids. Iterative cycling of the selection/amplification steps allows selection of one or a small number of nucleic acids which interact most strongly with the target from a pool which contains a very large number of nucleic acids. Cycling of the selection/amplification procedure is continued until a selected goal is achieved. In the present invention, the SELEX methodology is employed to obtain nucleic acid ligands to the Taq and Tth polymerases.

The SELEX methodology is described in the SELEX Patent Applications.

"Target" means any compound or molecule of interest for which a ligand is desired. A target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, etc. without limitation. In this application, the target is a DNA polymerase. In a preferred embodiment the DNA polymerase is Taq polymerase and Tth polymerase.

A "Labile ligand" as used herein is a nucleic acid ligand identified by the SELEX process that has a greatly decreased affinity for its target based on an adjustment of an environmental parameter. In the preferred embodiment, the environmental parameter is temperature, and the affinity of a ligand to its target is decreased at elevated temperatures.

"DNA Polymerase" as used herein refers to any enzyme which catalyzes DNA synthesis by addition of deoxyribonucleotide units to a DNA chain using DNA or RNA (reverse transcriptase) as a template. Thermostable DNA polymerases are isolated from microorganisms which thrive in temperatures greater than 40° C.

A "Switch" refers to any compound which functions to turn a reaction "on" or "off" depending upon some specific reaction condition(s). In the present invention the nucleic acid ligands function to turn the PCR "on" or "off" depending upon the temperature of the reaction. A switch can operate on the basis of other reaction conditions including pH, ionic strength or the presence or absence of specific ions. Nucleic acid switches are identified via the SELEX method by the appropriate selection of partitioning techniques. Partitioning parameters are determined in order that nucleic acids are selected that have the desired switching characteristics.

In the present invention, a SELEX experiment was performed in order to identify nucleic acid ligands with specific high affinity for the Taq and Tth polymerases from a degenerate library containing 30 random positions (30N) (Example 1). Although RNA or DNA ligands could be identified for this purpose, the examples below describe the identification of DNA ligands. The SELEX experiment was designed to identify oligonucleotides that bind and inhibit the polymerases at low temperature (room temperature), but not at higher temperatures (>40° C.). This was accomplished by using the target polymerase to amplify affinity-selected molecules in PCR at an elevated temperature. Under such conditions, DNA sequences that inhibit the Taq and Tth polymerases at high temperature were not expected to amplify and propagate during selection. This invention includes the specific ssDNA ligands to Tth polymerase shown in Table 2 (SEQ ID NOS:7–35) and Taq polymerase shown in Table 3 (SEQ ID NOS:36–66, 76, 77) and the nucleic acid ligands shown in Tables 4 and 5 (SEQ ID NO:67–74), identified by the methods described in Example 1. This invention further includes DNA ligands to Taq and Tth polymerase that inhibit the function of Taq and Tth polymerase.

The scope of the ligands covered by this invention extends to all nucleic acid ligands of the Taq and Tth polymerases, modified and unmodified, identified according to the SELEX procedure. More specifically, this invention includes nucleic acid sequences that are substantially homologous to the ligands shown in Tables 2–5. By substantially homologous it is meant a degree of primary sequence homology in excess of 70%, most preferably in excess of 80%. A review of the sequence homologies of the ligands of Taq and Tth shown in Tables 2–5 shows that sequences with little or no primary homology may have substantially the same ability to bind Taq and Tth polymerase, respectively. For these reasons, this invention also includes nucleic acid ligands that have substantially the same ability to bind the Taq and Tth polymerases as the nucleic acid ligands shown in Tables 2–5. Substantially the same ability to bind Taq or Tth polymerase means that the affinity is within a few orders of magnitude of the affinity of the ligands described herein. It is well within the skill of those of ordinary skill in the art to determine whether a given sequence—substantially homologous to those specifically described herein—has substantially the same ability to bind Taq and Tth polymerase, respectively.

This invention also includes the ligands as described above, wherein said ligands inhibit the function of other thermostable DNA polymerases, including, but not limited to, the Stoffel fragment, Tbr polymerase, Tlf polymerase and M-MLV reverse transcriptase.

This invention also includes the ligands as described above, wherein certain chemical modifications are made in order to increase the in vivo or in vitro stability of the ligand or to enhance or mediate the binding or other desirable characteristics of the ligand or the delivery of the ligand. Examples of such modifications include chemical substitutions at the sugar and/or phosphate and/or base positions of a given nucleic acid sequence. See, e.g., U.S. patent application Ser. No. 08/117,991, filed Sep. 8, 1993, entitled High Affinity Nucleic Acid Ligands Containing Modified Nucleotides now abandoned (See U.S. patent application Ser. No. 08/430,709, filed Apr. 27, 1995, entitled "High Affinity Nucleic Acid Ligands Containing Modified Nucleotides," now U.S. Pat. No. 5,660,985), which is specifically incorporated herein by reference. Other modifications are known to one of ordinary skill in the art. Such modifications may be made post-SELEX (modification of previously identified unmodified ligands) or by incorporation into the SELEX process.

The nucleic acid ligands to the Taq and Tth polymerases described herein are useful as reagents in the Polymerase Chain Reaction.

The present invention includes an improved method for performing the Polymerase Chain Reaction, wherein a sample containing a nucleic acid sequence that is to be amplified is mixed with 1) primers that are complementary to sequences that flank the sequence to be amplified, 2) a thermostable polymerase, and 3) a nucleic acid ligand that is capable of inhibiting the polymerase at ambient temperatures. The nucleic acid ligand inhibitor may be immobilized on a solid support. The normal steps of PCR are then followed—melting, annealing and synthesis—by thermal cycling of the mixture. The presence of the nucleic acid ligand prevents the mixture from amplifying background DNA by preventing any synthesis at lowered temperatures prior to or during cycling. The present invention also includes a PCR kit comprising a thermostable DNA polymerase and a nucleic acid ligand that inhibits said polymerase at ambient temperatures, yet allows synthesis to occur during the elevated temperature cycles of the PCR process. The present invention also includes a method for improving PCR, as understood by those skilled in the art, including the step of adding to the thermostable polymerase a nucleic acid ligand that inhibits said polymerase at ambient temperatures yet allows synthesis to occur during the elevated temperature cycles of the PCR process.

Nucleic Acid Ligands to Tag and Tth Polymerase.

Example 1 describes the experimental procedures used in the selection of nucleic acid ligands to both the Taq and Tth polymerases. The ss-DNA sequences obtained from 10 rounds of selection performed with Tth polymerase are set forth in Table 2. Twenty nine individual clones were sequenced from the Tth polymerase selection (only the variable 30 nucleotide region is shown in Table 2). The ligands were grouped into families based upon primary sequence homology.

The ss-DNA sequences obtained from 12 rounds of selection performed with Taq polymerase are set forth in Table 3. Of forty two sequences analyzed from the Taq polymerase selection, thirty three were unique. The upper case letters depict the 30-nucleotide random region that is flanked by the 5'-TTCTCGGTTGGTCTCTGGCGGAGC- and -TCTTGTGTATGATTC GCTTTTCCC-3' fixed sequence regions to form full-length sequences. The lower-case letters in some of the sequences depict the 5'-fixed sequence. The number of clones carrying the same sequence is indicated in parenthesis. The sequences were grouped into three families based on sequence similarity. Conserved sequence motifs in families I and II are boxed. Both families contained a different consensus sequence; 5'-A/$_G$A/$_G$TGT G/$_A$CAGTAT/$_G$C-3' for Family I and 5'-A/$_G$CGTTTTG-3' for Family II. In Family I, the 5' and the 3' regions of the consensus sequence showed potential for base pairing with each other (underlined in Table 3). Additionally, the covariation observed in these regions suggests the existence of a possible stem loop structure. In most of the ligands the potential base pairing regions extend beyond the consensus region. In contrast, Family II ligands do not have an obvious secondary structural motif.

Figure 3A:
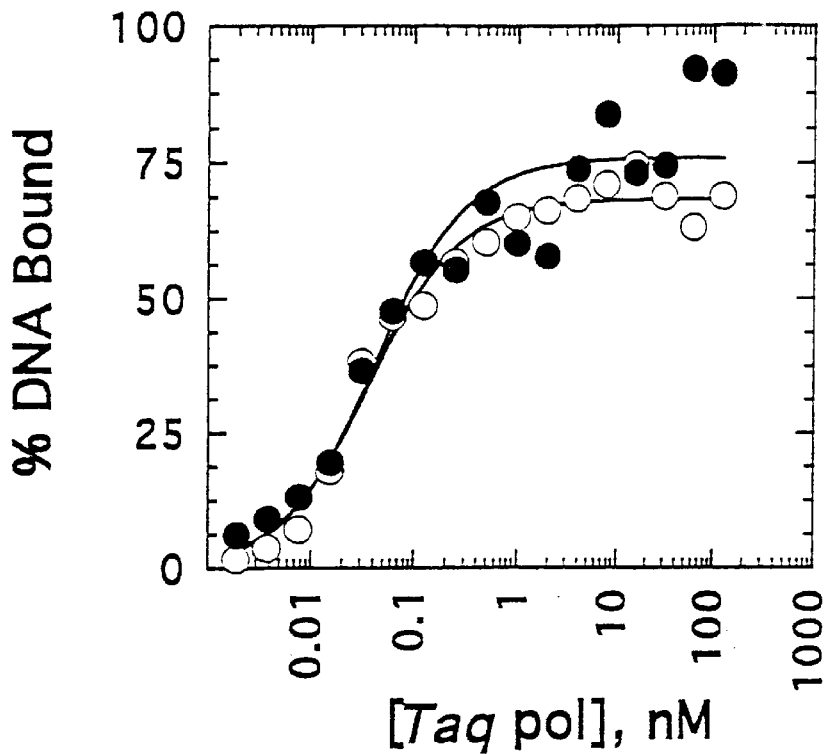
FIG. 3A depicts a binding curve for ligand 30 (●) and ligand 21 (○) to Taq polymerase.
Figure 3B:
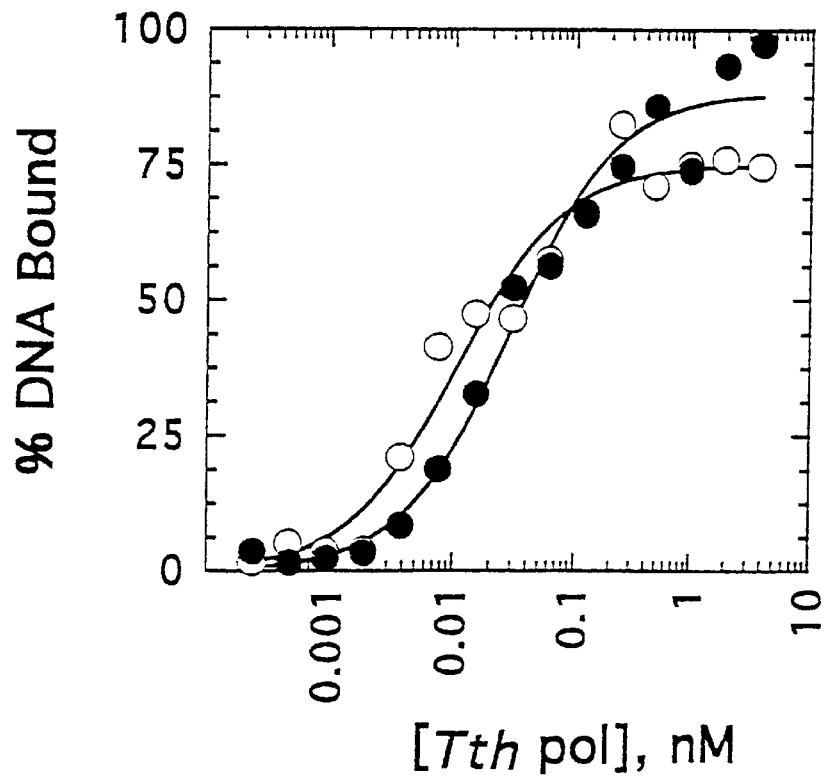
FIG. 3B depicts a binding curve for ligand 30 (●) and ligand 21 (○) to Tth polymerase.

Representative binding curves of clone 30 (TQ30 (SEQ ID NO:50)) from Family I and clone 21 (TQ21 (SEQ ID NO:59)) from Family II, are shown in FIG. 3. In both cases, the ligands show tight binding to the two polymerases, with $K_d$ values in the low picomolar range; $K_d$ values of TQ30 are 40±1 pM for Taq polymerase and 28±4 pM for Tth polymerase, whereas those of TQ21 are 36±4 pM and 10±2 pM for Taq polymerase and Tth polmerase, respectively. Several more ligands from the two families were screened. $K_d$ values ranged from 0.04 to 9 nM for Taq polymerase and from 0.01 to 0.3 nM for Tth polymerase.

Polymerase Inhibition Assays: Taq and Tth Polymerase.

Example 2 (FIGS. 5–9) describes a number of polymerase inhibition assays and demonstrates that the ligands of the invention are capable of inhibiting the interaction of both the Taq and Tth polymerases, at temperatures less than 40° C. In Example 2, the designed hairpin DNA (DNA-HP; 5'-ATGCCTAAGTTTCGAACGCGGCTAGCCAGCTTTT GCTGGCTAGCCGCGT-3' (SEQ ID NO:6) is used as a template for measurement of the ability of the enriched pools of DNA, as well as, ligands TQ30 (SEQ ID NO:50) and TQ21 (SEQ ID NO:59) from the Taq polymerase selection, to inhibit polymerase activity, under a variety of conditions. This assay detects template-directed fill-in synthesis of 15 nucleotides on a fold-back DNA hairpin.

Figure 5A:
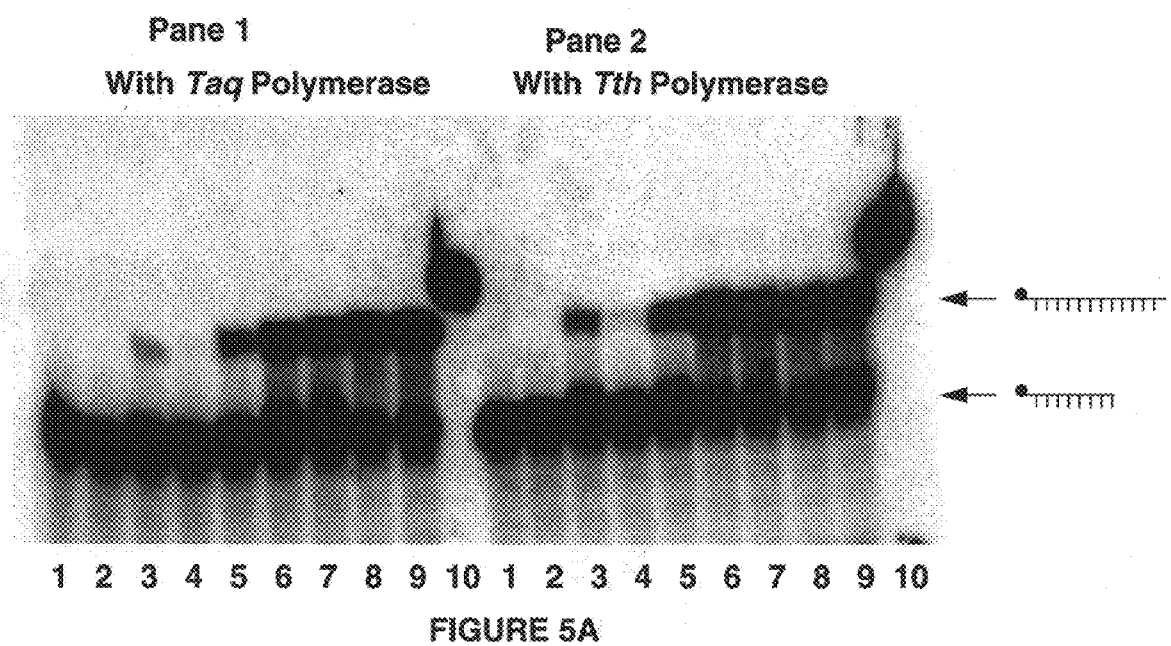
FIG. 5A illustrates a polymerase activity assay for the Taq and Tth polymerases carried out at different temperatures with different times of incubations. The DNA is resolved on a 15% polyacrylamide gel under denaturing conditions. The data on Panel 1 were obtained with the Taq polymerase and the enriched pool selected for Taq polymerase, whereas those shown on Panel 2 were obtained with the Tth polymerase and the enriched pool selected for Tth polymerase. The untreated, 5'-end labeled DNA hairpin template (lane 1); the labeled template in a reaction mixture that lacks the polymerase (lane 2); incubation of the complete reaction mixture for 25 minutes at room temperature in the absence of (lane 3) and in the presence of the enriched pool (lane 4). Lanes 5, 6, and 7 show the incubations of complete reaction mixtures in the presence of the enriched pool for 5 minutes at 37° C., 50° C. and 60° C., respectively. Lanes 8 and 9 show the incubations of the complete reaction mixtures in the presence (lane 8) and absence (lane 9) of the enriched pool at 70° C. for 5 minutes. Lane 10 shows the gel mobility of the end-labeled pool DNA. The schematics on the right of the gels depict the positions of the starting short end-labeled DNA and the polymerase extended product.

FIG. 5A shows the results of inhibition assays carried out at different temperatures with different times of incubations using the enriched pools of DNA ligands. The activity of both the Taq and Tth polymerases is generally low at low temperatures and increases as the temperature is increased, as can be seen by comparing lane 3 (room temperature reaction) with lanes 6–9 (reaction at 50, 60 and 70° C., respectively). The enriched pools inhibit the activity of their respective polymerases at room temperature (lane 4), but not at 50° C.–70° C. Lane 10 shows the mobility of the radiolabeled pool as a reference to detect the possible extension of DNA molecules in the pool that can serve as a template for the polymerases. The lack of radiolabeled bands migrating closer or above the labeled pool in lanes 6–9 indicates the absence of polymerization of the ssDNA pool.

Figure 5B:
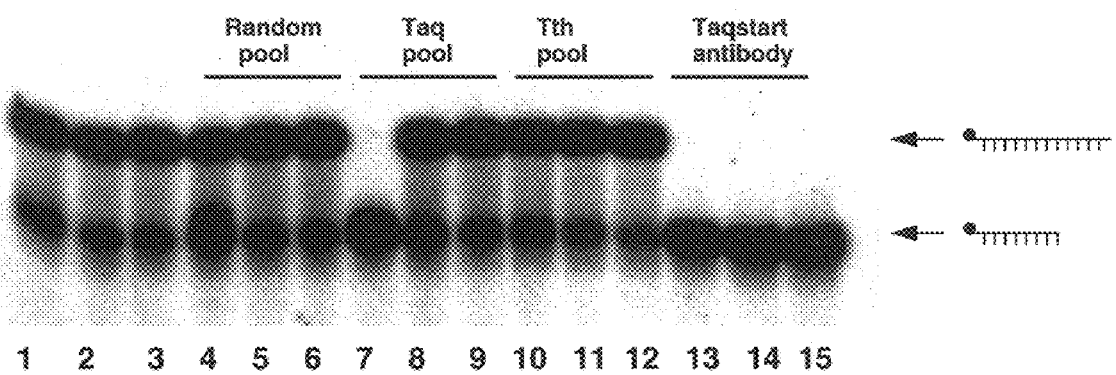
FIGS. 5B and 5C illustrate a second polymerase activity assay for the Taq and Tth polymerases, performed at three different temperatures. The DNA is resolved on a 15% polyacrylamide gel under denaturing conditions. The data in FIG. 5B were obtained with the Taq polymerase and the data in FIG. 5C were obtained with the Tth polymerase. Lanes 1–3 show the products obtained in the absence of any inhibitor upon incubation at room temperature, 30° C. and 37° C., respectively, for 5 minutes. Lanes 4–6 show the data obtained with the unselected random sequence pool; lanes 7–9 with the enriched pool for Taq polymerase; lanes 10–12 with the enriched pool for Tth polymerase; lanes 13–15 with Taqstart antibody for 5 minute incubations at the three temperatures indicated. The schematics on the right indicate the starting short end-labeled DNA and the polymerase extended product.
Figure 5C:
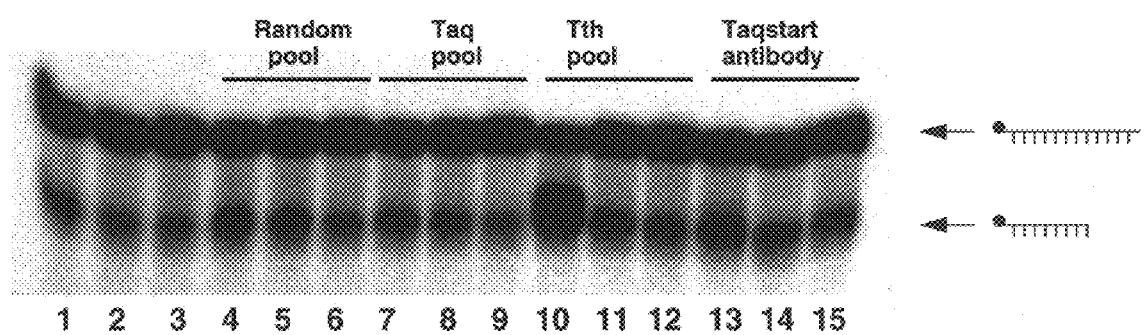
Figure 6A:
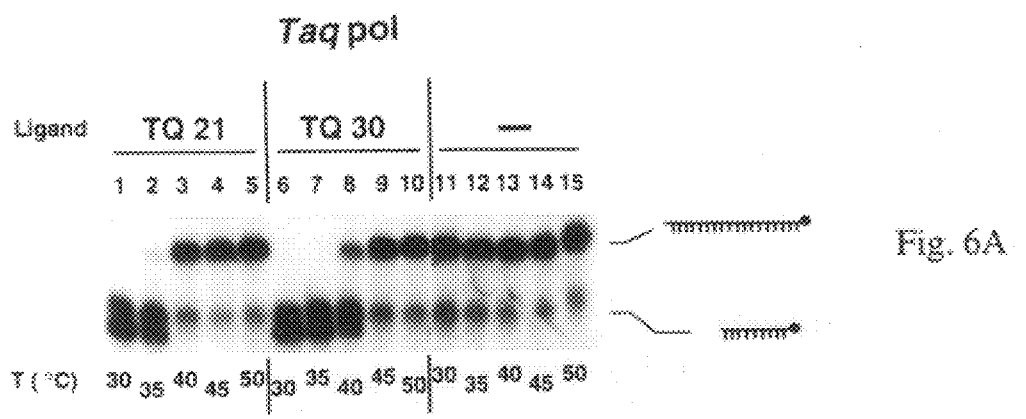
FIGS. 6A–6D depict the effect of temperature on the inhibition of Taq polymerase (FIG. 6A) and Tth polymerase (FIG. 6B) by ligands TQ30 (SEQ ID NO:50) and TQ21 (SEQ ID NO:59) (lanes 1–10). The DNA is resolved on a 10% polyacrylamide gel under denaturing conditions. Lanes 11–15 depict the formation of product in the absence of an inhibitor. The right side of the autoradiograms schematically depict the 5'-labeled template before and after polymerase extension.
Figure 6B:
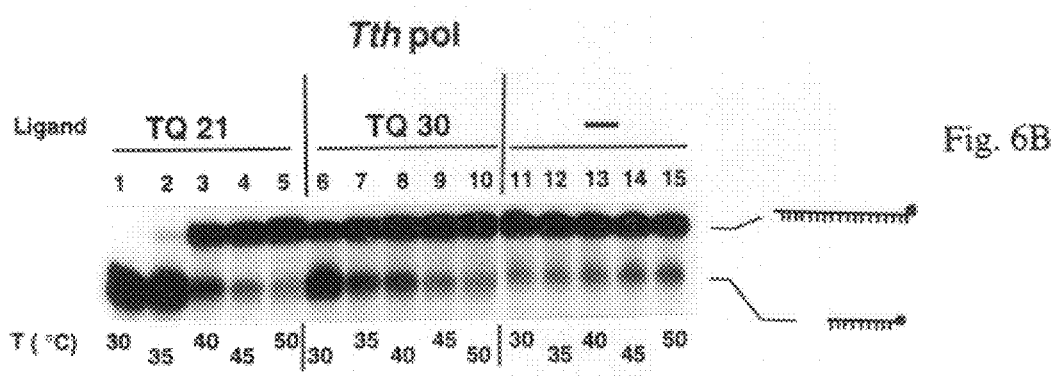
Figure 6C:
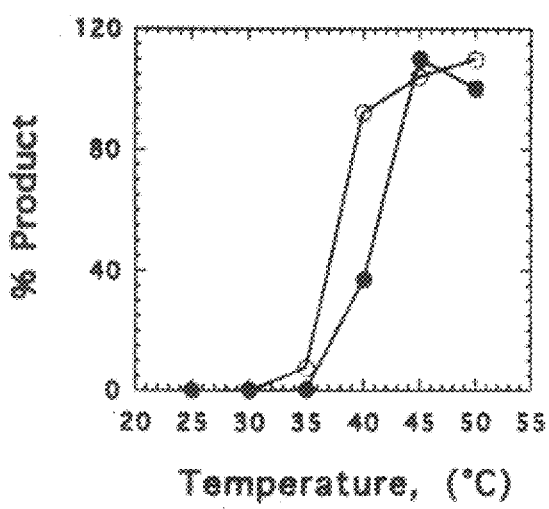
Figure 6D:
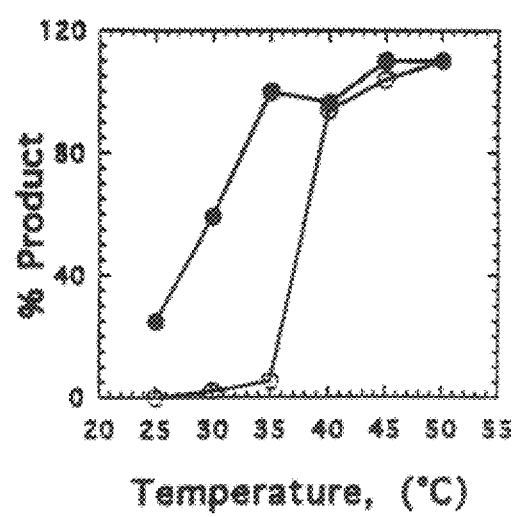

Since the activity of thermostable polymerases is low at ambient temperature, the incubation period in the assay was increased to 16 hours. FIGS. 5B and 5C show the results of 16 hour incubation of the template with the two polymerases in the presence of selected pools and the random pool. In addition, the inhibition mediated by selected pools was compared to that of anti-Taq antibody (TaqStart). The data in FIG. 5B was obtained with the Taq polymerase and the data in FIG. 5C was obtained with the Tth polymerase. Over the three temperatures studied, room temperature, 30° C. and 37° C., the random pool did not show inhibition of the two polymerases (compare lanes 1–3 with 4–6), suggesting that the inhibition caused by the enriched pool is sequence specific. The pool selected for Taq polymerase completely inhibited the polymerase activity over a 16 hour incubation only at room temperature (lane 7), but not at 30° C. and above (lanes 8 & 9). Although the pool selected for Tth polymerase did show binding to Taq polymerase, it was unable to inhibit Taq polymerase (lanes 10–12). As expected, Taqstart antibody inhibited the polymerase activity at all three temperatures investigated (lanes 12–15). The ssDNA pool selected for Tth polymerase, however, did not inhibit the enzyme activity over a 16 hour incubation (compare lanes 1–3 with 4–6). In contrast, the same pool was able to inhibit the enzyme activity over short periods of incubation. The pool selected for Taq polymerase was able to partially inhibit (>50%) the Tth activity over 16 hour incubation at room temperature (lane 10). Taqstart antibody did not have any effect on the activity of Tth (lanes 13–15).

The use of Taqstart antibody is limited to one time in a PCR reaction. Once it is denatured at high temperature it cannot renature back to its native form. Nucleic acid ligands with simple secondary structures, however, have the potential to renature back to their native form after going through a thermal cycle. An experiment was carried out to investigate whether the inhibitory capacity of the DNA pool selected for Taq polymerase can be restored after heating (FIGS. 5D and 5E). FIG. 5D shows the inhibition of Taq activity between 20° C.–40° C. by the selected DNA pool that has not been subjected to thermocycling. Over 45 minutes of incubation, the pool completely inhibits Taq activity at 20° C. and 25° C. Within this relatively short period of incubation, the pool exhibited >70% inhibition at 30° C. A very similar inhibition profile can be seen with the DNA pool that has been subjected to two PCR cycles with the Taq polymerase in the absence of the template DNA. This result demonstrates that the inhibition mediated by ssDNA is reversibly temperature sensitive and can be restored even after PCR.

FIG. 6 shows the temperature range in which sequences, TQ30 (SEQ ID NO:50) and TQ21 (SEQ ID NO:59) (Table 3), are inhibitory toward the Taq and Tth DNA polymerases. The hairpin extension assays depicted in this figure were performed at the indicated temperatures for 1 hour using 250 nM of the respective ligand (lanes 1–10). As anticipated, the ssDNA ligands did not inhibit either DNA polymerase at temperatures >40° C. (FIGS. 6A and 6B). The temperatures at which 50% of the product is generated during the one-hour assay ($IT_{50}$ values) for ligand TQ30 are 41° C. and 29° C. for Taq polymerase and Tth polymerase, respectively. The respective values for ligand TQ21 are 37° C. and 29° C. Binding affinities of the two ligands for these polymerases decrease at higher temperatures (data not shown), in agreement with their decreased inhibitory activity at high temperature. In the hairpin extension assays, approximately 2% of the input hairpin template was not extended by DNA polymerase, presumably due to incorrect folding.

Figure 7A:
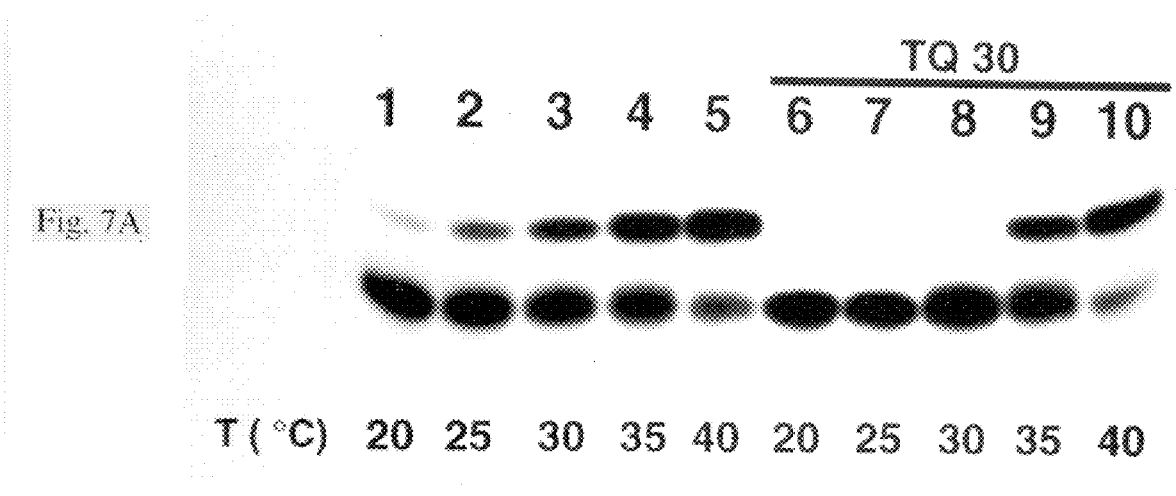
FIG. 7 illustrates the reversible inhibition of Taq polymerase by ligand TQ30 (SEQ ID NO:50). The DNA is resolved on a 10% polyacrylamide gel under denaturing conditions. Lanes 1–5 show the products obtained in the absence of any inhibitor upon incubation between 20° C.–40° C. Lanes 6–10 show the products formed upon incubation between 20° C.–40° C. in the presence of ligand TQ30 that had not been thermocycled (FIG. 7A) and ligand TQ30 that had been subjected to 25 rounds of thermocycling (FIG. 7B).
Figure 7B:
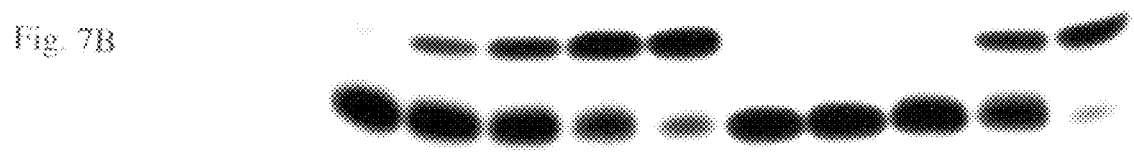

FIG. 7 illustrates that the inhibition of Taq polymerase by ligand TQ30 (SEQ ID NO:50) is thermally reversible and can be restored even after PCR. The hairpin template extension assays depicted in this figure were performed at the indicated temperatures for 10 minutes in a 100 μL reaction volume with 5 U of Taq polymerase, in the absence (lanes 1–5) and in the presence of ligand TQ30 (50 nM) (lanes 6–10). In FIG. 7A, ligand TQ30 had not been subjected to thermocycling. In FIG. 7B, ligand TQ30 was subjected to 25 rounds of thermocycling with Taq polymerase (30 seconds at 90° C.; 1 minute at 50° C., 30 seconds at 72° C.) and cooled to room temperature before adding the radiolabeled hairpin template (250 nM). As can be seen in FIG. 7, in both cases ligand TQ30 inhibited the polymerase at temperatures below 40° C. Additionally, the sample that underwent thermocycling showed identical or more effective inhibition than the sample not subjected to thermocycling.

Figure 8A:
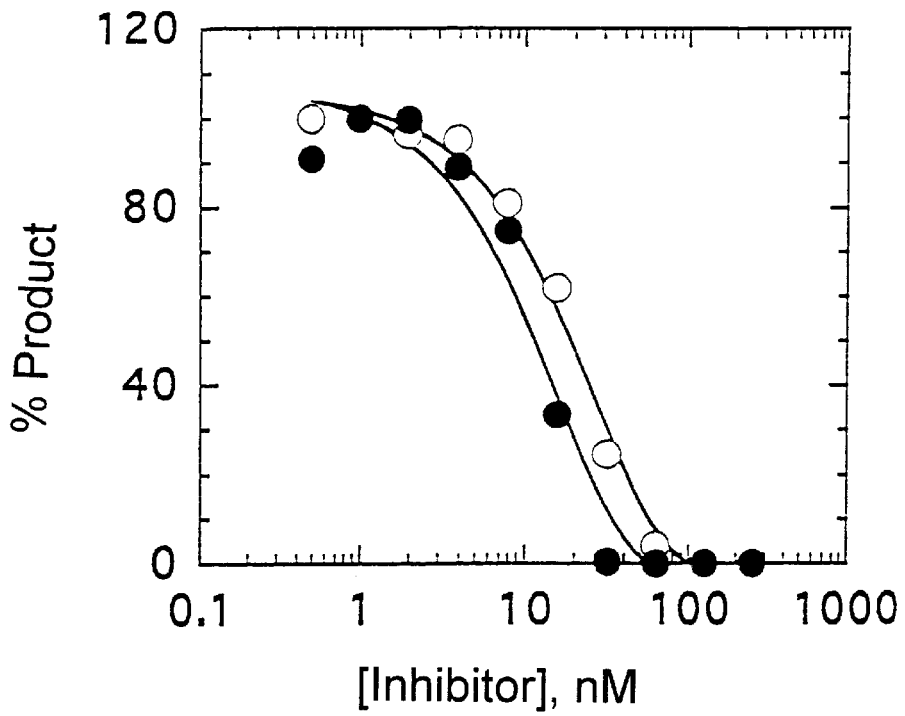
FIGS. 8A and 8B depict the effect of ligand concentration on the inhibition of Taq polymerase (FIG. 8A) and Tth polymerase (FIG. 8B) by ligands TQ30 (SEQ ID NO:50) (●) and TQ21 (SEQ ID NO:59) (○). The amount of product formed in the presence of varying concentrations of inhibitor in the template extension assays was quantitated by phosphorimager and normalized to the amount of product formed in the absence of an inhibitor to obtain the percent product (abscissa).
Figure 8B:
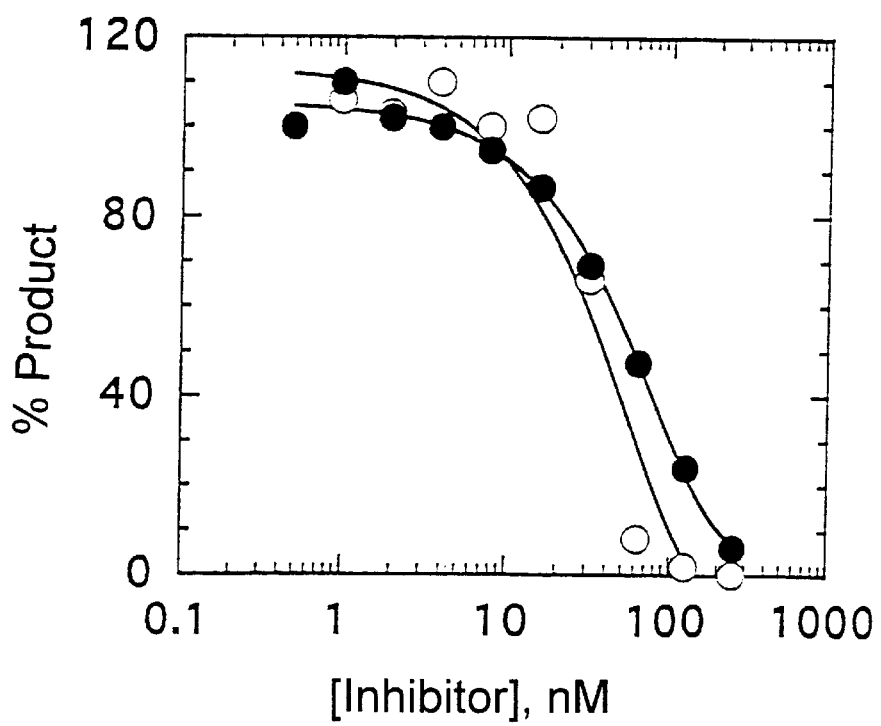
Figure 9:
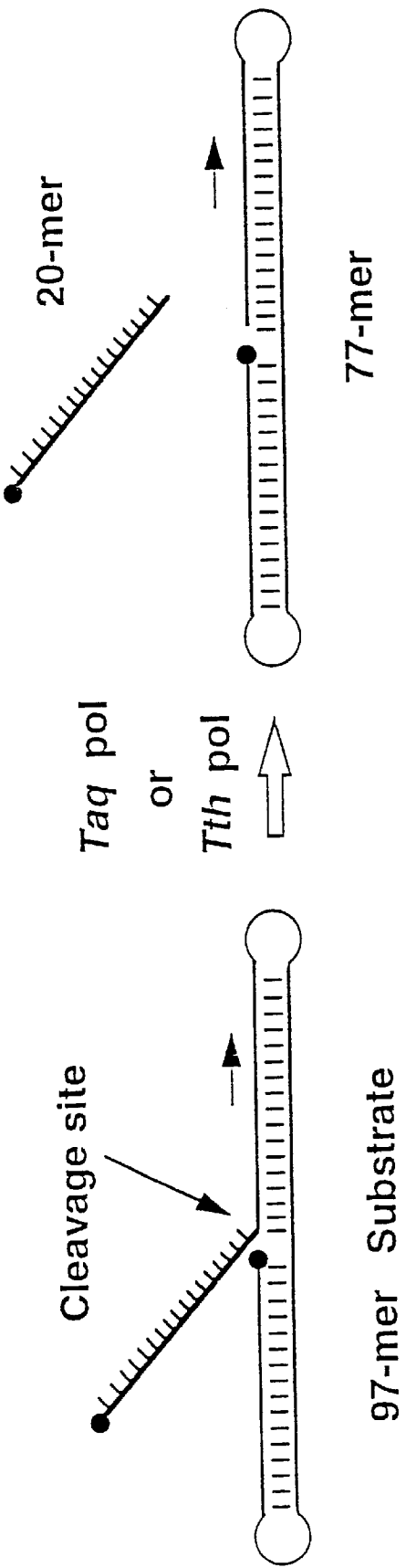
FIG. 9 illustrates schematically cleavage of the 97-nucleotide DNA sequence (Exo-Sub) (5'-TTCGAGCGTGAATCTGAATTCGCG-GCTAGCCAGCCAGCTTTTGCTG GCTAGCCGCG-GTGGGAAACTGAGGTAGGTGTTTTCACCTACCTCAG TTTCCCACC-3' (SEQ ID NO:75)), with predicted two stem-loops with a displaced strand, catalyzed by the 5'→3' exonuclease activity of Taq and Tth polymerase. Polarity of the folded sequence is indicated by the small arrow. The cleavage mediated by the exonuclease activity of the DNA polymerases is expected to occur near the junction of the displaced strand and the helix, resulting in two DNA fragments of 20-nucleotides and 77-nucleotides. Solid circles at the two ends of the molecule indicate radiolabels.

FIG. 8 demonstrates the effect of ligand concentration on the inhibition of the Taq and Tth polymerases. The concentration of inhibitor required to produce 50% of the product in the hairpin assay ($IC_{50}$ values) for TQ30 (SEQ ID NO:50) and TQ21 (SEQ ID NO:59) were 6.5 nM and 10 nM, respectively, for inhibition of Taq polymerase at room temperature (approximately 22° C.) over a 16 hour incubation (FIG. 8A). Since the concentration of Taq polymerase used in the assay is 12.5 nM, enzyme inhibition by TQ30 (SEQ ID NO:50) is likely to be a result of stoichiometric binding. When assayed at 30° C. over 1 hour, $IC_{50}$ values increased by approximately three fold (22 nM for TQ30 and 67 nM for TQ21; data not shown). The $IC_{50}$ values of TQ30 and TQ21 for the inhibition of Tth polymerase were 60 and 36 nM, respectively, at room temperature (FIG. 8B). Overall, these oligonucleotides are more effective inhibitors for Taq polymerase, the enzyme used in selection, than for Tth polymerase.

To rule out the possibility that the observed inhibition of the extension of the template is due to preferential binding of selected ligands to the polymerase and subsequent utilization as substrates, 5'-end radiolabeled TQ21 and TQ30 ligands were incubated with the two DNA polymerases for 16 hours (Example 2, data not shown). Ligand TQ30 did not show extension products upon incubation with either enzyme, indicating that it is not a substrate for the polymerase activity. TQ21, however, gave a higher molecular weight band indicating sequence extension upon incubating with both polymerases. The observed partial extension of ligand TQ21 was effectively eliminated by blocking the availability of the 3' OH group by capping the 3' end with an ethylene glycol linker using standard conditions. The 3'-capped oligonucleotide constructs are equally effective inhibitors as the uncapped molecules (data not shown). These results indicate that the ssDNA ligands are poor substrates for polymerase activity and that the two types of ligands are likely positioned on DNA polymerases differently; TQ21 binds to the polymerases such that its 3' end can be extended (albeit poorly), whereas TQ30 cannot extended upon binding.

Affinity Capture Experiment.

The thermal reversibility of the interaction of nucleic acid ligands with the Taq and Tth polymerases raises the possibility of the use of an affinity matrix generated with such ligands, to capture the polymerase after one amplification, for reuse in a subsequent amplification. To investigate the possibility of affinity capture, affinity beads containing ligands TQ30 (SEQ ID NO:50) and TQ21 (SEQ ID NO:59) were prepared as described in Example 1. After extension of the hairpin template with Taq and Tth polymerases in a PCR buffer containing heparin the reaction was mixed with either affinity beads or control beads as described in Example 2, the beads were washed thoroughly and then exposed to a fresh aliquot of reaction mixture containing all of the reagents, except the polymerase. After incubating for an additional 5 minutes at 70° C. to allow the extension on the newly added template, the reaction mixtures were analyzed on an 8% polyacrylamide gel under denaturing conditions. In reaction mixtures that contained the control beads there is no extension of the template in the second round of amplification. In contrast, there is no difference in the extension products in both first and the second rounds of amplification in the reaction mixtures that contained affinity beads, indicating that the affinity beads containing both, ligand TQ30 (SEQ ID NO:50) and TQ21, successfully captured the two polymerases after the first round of PCR.

Effect of Ligands TQ30 and TQ21 on the Exonuclease Activity of Taq and Tth Polymerase.

As discussed above, in addition to their ability to catalyze polynucleotide synthesis, both Taq and Tth polymerase also possess 5'→3' exonuclease activity (Joyce and Steitz (1987) Trends Biochem. Sci. 12:288; Longley et al. (1990) Nucleic Acids Res. 18:7317). The preferred substrate for the 5'→3' exonuclease activity is a displaced ssDNA (or a fork-like structure) with cleavage occuring near the duplex/ssDNA junction. To study the effect of the oligonucleotide inhibitors on the 5'→3' exonuclease activity of the polymerases, DNA substrate (Exo-Sub) containing a displaced ssDNA in a hairpin was designed (Example 3, FIG. 9). Radiolabeling the Exo-Sub substrate at both the 5' and 3' ends allowed detection of the two DNA fragments produced by the exonuclease activity. The two labeled DNA fragments originating from the exonuclease activity appeared both in the presence and absence of the oligonucleotide inhibitors (data not shown), however, the amount of cleavage products generated in the presence of the oligonucleotide inhibitors was somewhat lower than that produced in the absence of inhibitors, indicating that oligonucleotide inhibitors exert some inhibitory effect toward the exonuclease activity of the enzymes. Since these oligonucleotides completely inhibited the polymerase activities of the two enzymes at 250 nM, their effect on exonuclease activity is considered marginal.

Inhibition of other DNA Polymerases.

Inhibition assays using several other commercially available DNA polymerases and ligands TQ21 (SEQ ID NO:59) and TQ30 (SEQ ID NO:50) as inhibitors are described in Example 4. Four thermostable enzymes (Tbr polymerase from *Thermus brockianus*, Tfl polymerase from *Thermus flavus*, Tma polymerase from *Thermotoga maritima* and Tli polymerase from *Thermococcus litoralis*); three mesophilic enzymes (Klenow fragment of *E.coli* DNAP1 (KF), T4 DNA polymerase and T7 DNA polymerase); and four reverse transcriptases (RT) (HIV-I RT, AMV (avian myeloblastosis virus) RT and M-MLV (moloney murine leukemia virus) RT and its mutant lacking RNase H activity (SuperScript II) were examined.

Of the six thermostable polymerases examined (including Taq and Tth polymerase), the four polymerases derived from Thermus species (Taq, Tth, Tbr and Tlf) were inhibited by both of the selected oligonucleotides, suggesting that these enzymes share a high degree of similarity. As stated above, Tth polymerase and Taq polymerase are reported to be 93% similar and 88% identical at the amino acid sequence level (Abramson (1995) in *PCR Strategies* (Academic Press, New York). Tfl polymerase is reported to be 93% similar and 86% identical to Taq polymerase at the amino acid level (D. Gelfand, personal communication). Tma polymerase from *Thermotoga maritima* and Tli polymerase from *Thermococcus litoralis*, on the other hand, were not inhibited by either of the ligands. Tli polymerase shares little sequence homology with eubacterial enzymes (Ito and Braithwaite (1991) Nucleic Acids Res. 19:4045). Tma polmerase is reported to be 61% similar and 44% identical to Taq polymerase at the amino acid level (Abramson (1995) in *PCR Strategies* (Academic Press, New York), yet the oligonucleotide ligands do not inhibit Tma polymerase.

Of the four reverse transcriptases tested, RTs from HIV-I and AMV (avian myeloblastosis virus) were not inhibited. On the other hand, RT from M-MLV (moloney murine leukemia virus) and its mutant lacking RNase H activity (SuperScript II) were inhibited by the two oligonucleotide ligands.

Mesophilic DNA polymerases, such as, Klenow fragment of *E.coli* DNAP1 (KF), T4 DNAP and T7 DNAP were not inhibited by either ligand at 0.5 µM concentration, despite the similarity of the polymerase domains of Taq polymerase and KF (Kim et al. (1995) Nature (London) 376:612; Lawyer et al. (1989) J. Biol. Chem. 264:6427). Thus, it appears that the oligonucleotide inhibitors are generally fairly specific. These results are similar to the behavior of nucleic acid ligands identified by in vitro selection for other Reverse transcriptases (Tuerk and MacDougal (1994) Proc. Natl. Acad. Sci, U.S.A. 89:6988; Chen and Gold (1994) Biochemistry 33:8746; Schneider et al. (1995) Biochemistry 34:9599).

Amplification of Low Copy Number Targets.

Figure 10A:
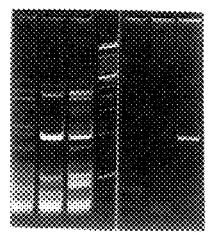
FIGS. 10A–10C illustrate the detection of a low copy number target using standard PCR amplification, "hot start" PCR and PCR amplification in the presence of oligonucleotide inhibitors TQ30 and TQ21 ("NeXstart PCR").
Figure 10B:
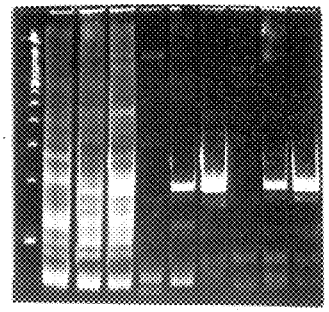
Figure 10C:
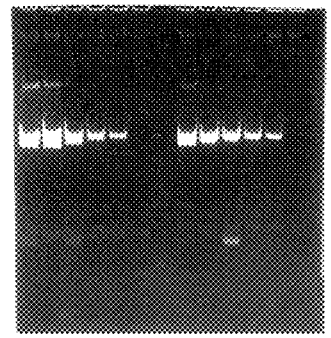

Example 5 (FIG. 10) describes a number of PCR amplifications comparing stardard PCR techniques, "hot start" PCR and PCR using the TQ30 and TQ21 to facilitate the detection of a low copy number target by PCR in the absence of "hot start" conditions. A primer-template system designed to detect a 203-base pair (bp) DNA fragment from the HIV-2 LTR (long terminal repeat) as described by Respess et al. (1994) in *Interscience Conference on Antimicrobial Agents and Chemotherapy* 94:110 was utilized. The PCR amplifications were carried out with 0, 10 and 50 copies of HIV-2 LTR target. Under normal PCR conditions, the identification of the correct target band was compromised by the presence of a number of nonspecific bands (FIG. 10A, lanes 1–3). Amplification carried out under "hot start" conditions eliminated the nonspecific bands (FIG. 10A, lanes 4–6). The results of amplification performed in the presence of a nonspecific 78-nucleotide ssDNA sequence containing identical 5'- and 3'-fixed sequences as TQ21 and TQ30 (FIG. 10B, lanes 1–3) were similar to those obtained by PCR without using "hot start" conditions. However, the addition of either TQ21 (FIG. 10B, lanes 4–6) or TQ30 (FIG. 10B, lanes 7–9) carried out under standard conditions (without "hot start") eliminated the nonspecific bands without affecting the yield of the target-specific band. Of particular importance was the observation that when the target copy number was low, signal detection was very efficient (FIG. 10B, compare lane 2 with lanes 5 and 8). The effect of oligonucleotide inhibitors was similar when Tth polymersase was used in place of Taq polymerase (data not shown) in detecting low copy number HIV-2 LTR. The enhanced yield of the target-specific band obtained with the oligonucleotide inhibitors in PCR increases the sensitivity of the reaction, facilitating detection of the target present with only approximately 3 copies (FIG. 10C).

The oligonucleotide inhibitors used in the experiment described in FIG. 10 were uncapped at their 3' ends, potentially permitting them to initiate amplification nonspecifically, and further complicating the outcome of PCR. However, no adventitious bands were detected, suggesting that in this system, 3'-capping of oligonucleotide inhibitors was not required to eliminate the generation of nonspecific bands.

Identification of Truncated Ligands of TQ30 and TQ21 with Inhibitory Activity.

Typically, not all nucleotides in a full-length sequence are necessary for its function. Identification of truncated DNA sequences that retain the function of the whole sequence, therefore, is desirable. Ligands TQ30 (SEQ ID NO:50) from Family I and TQ21 (SEQ ID NO:59) from Family II (see Table 4), were chosen for truncation experiments. Affinity selections on end-labeled nested fragments generated from the full-length sequences of both ligands, followed by sequencing gel analysis, as described in Example 2, did not give identifiable boundaries. The two ligands were therefore subjected to deletion analysis. Sequentially deleted forms were tested for their ability to inhibit polymerases in the hairpin extension assay to identify functional truncates.

Truncates of ligand TQ30 (SEQ ID NO:50).

The variable 30-nucleotide region of TQ30 containing the conserved sequence motif with the predicted stem-loop structure (Trnc.A-30 (SEQ ID NO:74); Table 5) inhibits Taq polymerase at 25° C. to the same extent as the full-length sequence (data not shown). At higher temperatures, however, the efficiency of inhibition is lower than the full-length sequence. At 30° C., for example, the inhibition of Taq polymerase by Trnc.A-30 (250 nM) is approximately 82%, whereas the full-length sequence completely inhibited the enzyme at this temperature and concentration. The increased thermal sensitivity of Trnc.A-30 may be due to the presence of an interrupted helix with A-T base pairs, a helix with propensity to melt at a low temperature.

Figure 11:
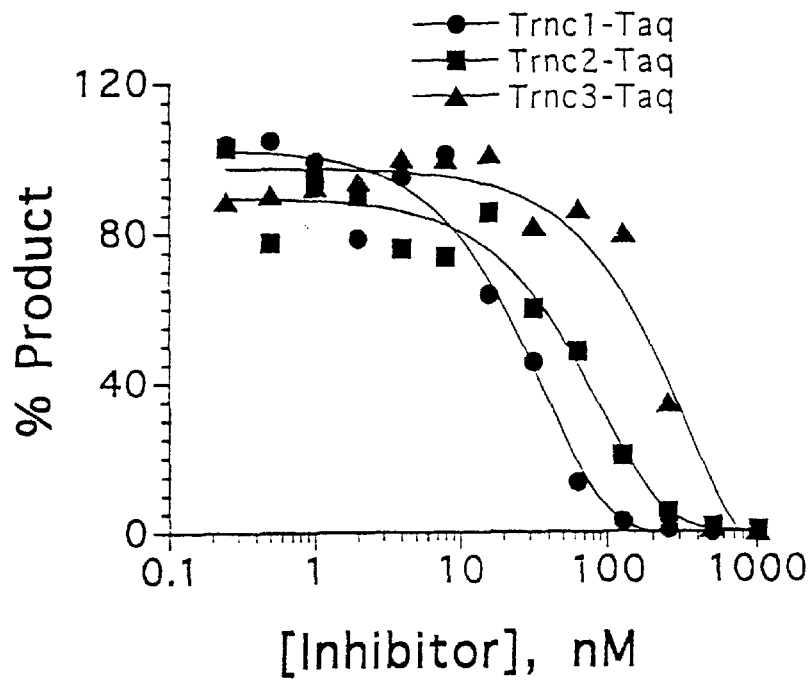
FIG. 11 depicts the effect of the concentration of truncated ligands Trunc.1-30 (SEQ ID NO:75) (●), Trnc.2-30 (SEQ ID NO:76) (■) and Trnc.3-30 (SEQ ID NO:77) (▲) on the activity of Taq polymerase. The amount of product formed in the presence of varying concentrations of inhibitor was quantitated by phosphorimager and normalized to the amount of product formed in the absence of an inhibitor to obtain the percent product (abscissa).

Three stem-loop variants of Trnc.A-30 containing uninterrupted stems with high G-C base pairs were therefore designed. In these variants the conserved sequence motif identified in Family I was unaltered (Table 5), but the stems had varying lengths. At 250 nM inhibitor concentration, Trnc.1-30 (SEQ ID NO:67) and Trnc.2-30 (SEQ ID NO:68) inhibited approximately 95% of the activity of Taq polymerase, whereas Trnc.3-30 (SEQ ID NO:69) inhibited only about 60% of the polymerase activity (see below). Trnc.3-30 containing the shortest stem (7-base pairs) of the three variants was a poor inhibitor for Taq polymerase, indicating that additional contacts in the stem are required for productive interaction. To determine whether the decreased inhibition observed with Trnc.3-30 is due to its reduced affinity to bind to the polymerase, the affinities of all three variants for binding to Taq polymerase were calculated. The $K_d$ values fell between 2–3 nM (Table 5), indicating that all three variants had similar binding affinities. Hence, the lack of inhibition caused by Trnc.3-30 was not due to lack of binding, but presumably due to its inability to block the active site. Affinities of the three variants for binding to Taq polymerase are about 75-fold lower than the full-length molecule ($K_d$ of the full-length sequence is 40 pM), and about 3–5-fold lower than Trnc.A-30. The $IC_{50}$ values for the three constructs decreased with the decrease in length of the stem; 25, 50 and 186 nM for Trnc.1-30, Trnc.2-30 & Trnc.3-30, respectively (FIG. 11). This result is in agreement with the notion that the ligands with longer stems are more effective inhibitors. The $IC_{50}$ value of the full-length sequence is 22 nM. Hairpin extension assays were preformed at 30° C. for 1 hour.

Although full length TQ30 inhibits Tth polymerase, neither Trnc.1-30 nor Trnc.2-30 inhibit Tth polymerase, despite the fact that the enzyme is completely inhibited by the full length ligand.

Figure 12:
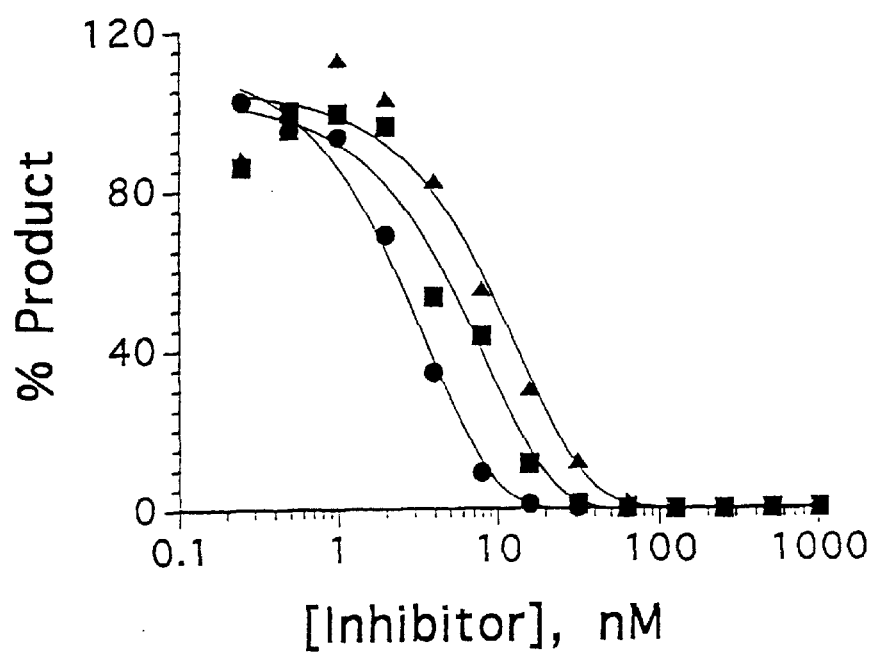
FIG. 12 depicts the effect of inhibitor concentration of truncated ligands Trunc.1-30 (●), Trnc.2-30 (■) and Trnc.3-30 (▲) on the activity of the Stoffel fragment. The amount of product formed in the presence of varying concentrations of inhibitor was quantitated by phosphorimager and normalized to the amount of product formed in the absence of an inhibitor to obtain the percent product (abscissa).

Stoffel fragment (61 kD) is a truncated form of Taq polymerase that lacks the 5'→3' exonuclease activity and is similar to 67 kD KlenTaq DNA polymerase (67 kD). The polymerase activity of the Stoffel fragment was completely inhibited by the full-length, as well as, the three truncated forms of TQ30. $IC_{50}$ values of the three truncates are Trnc.1-30=2.7 nM, Trnc.2-30=5.9 nM and Trnc.3-30=10.3 nM (FIG. 12). Overall, the three truncated forms of TQ30 are more effective in inhibiting the Stoffel fragment than Taq polymerase (compare FIG. 11 with FIG. 12). The $IC_{50}$ values of these truncates for the inhibition of the Stoffel fragment are an order of magnitude better than those for Taq polymerase. The $IT_{50}$ value for inhibition of the Stoffel fragment by Trnc.2-30 was 38° C. (data not shown). Surprisingly, the TQ21 sequence, which inhibits both Taq and Tth polymerase does not inhibit the Stoffel fragment. This suggests that the binding site of TQ21 on the Stoffel fragment is either partially or completely deleted or has been reorganized upon truncation of the protein.

Truncates of ligand TQ21 (SEQ ID NO:59).

Figure 13A:
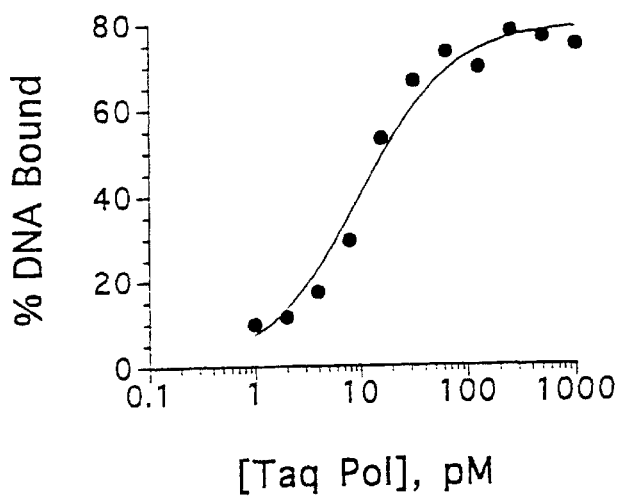
FIGS. 13A–13C illustrate the affinity and inhibition characteristics of truncated ligand Trnc.21 (SEQ ID NO:70).
Figure 13B:
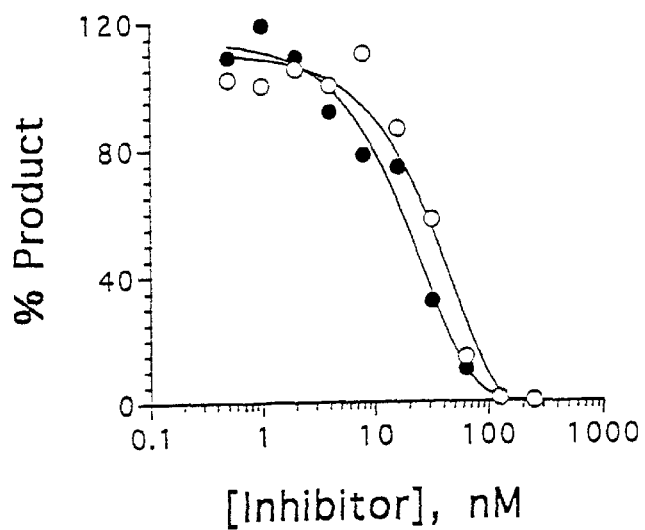
Figure 13C:
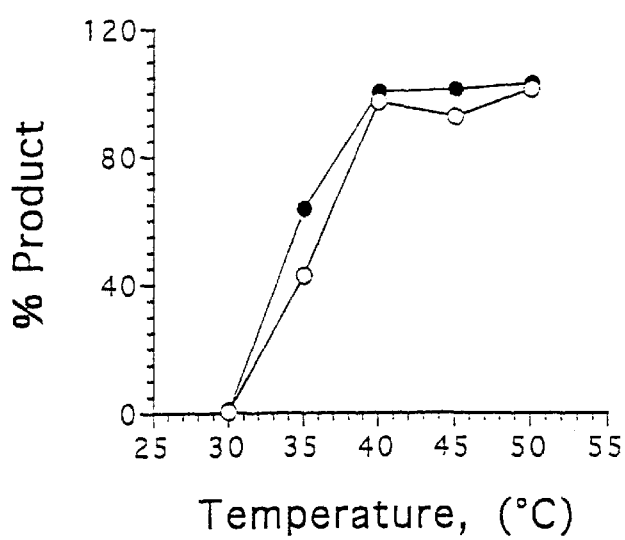

Unlike the Family I ligands, such as TQ30, the 30-nucleotide variable region of the Family II ligand, TQ21, does not inhibit either Taq or Tth polymerase (data not shown), indicating that the additional nucleotides from fixed regions are required for inhibition. Deletion analysis of the full-length TQ21 sequence led to the identification of a 51-mer sequence (Trnc.21 (SEQ ID NO:70) (Table 4)) that retained the ability to inhibit both Taq and Tth polymerases. In addition to the entire 30-nucleotide random region, the Trnc.21 sequence contained 9 and 12 nucleotides from the 5' and 3' fixed regions, respectively (Table 4). In contrast, to the TQ30 truncates, which showed decreased affinity for Taq polymerase, Trnc.21 showed increased affinity; the $K_d$ of Trnc.21 for binding to Taq polymerase is 9 pM (FIG. 13A), about 4-fold higher affinity than the full-length sequence. The $IC_{50}$ value of Trnc.21 for inhibition of Taq polymerase is 21 nM (FIG. 13B), about 3-fold lower than the value for the full-length sequence. The calculated $IT_{50}$ values for Taq polymerase and Tth polymerase are 34° C. and 35.6° C., respectively (FIG. 13C). The hairpin extension assays were carried out between the temperatures of 35 and 50° C. for 1 hour with 250 mM Trnc.21. Thus, based on the affinity and the values of $IC_{50}$ and $IT_{50}$, the truncated form of TQ21 is a better inhibitor than the full-length sequence. Similar to the full-length sequence, Trnc.21 did not inhibit the activity of the Stoffel fragment.

Dimeric Forms of Truncates.

Multimerization of ligands increases effective local concentration, resulting in a longer resident time with the target (avidity). Based on its moderate affinity for Taq polymerase Trnc.2-30 was selected for synthesis of a homodimer (Table 4). Homodimer (D.30-D.30) (SEQ ID NO:71) (Table 4) of Trnc.2-30 was synthesized in tail-to-tail orientation (linked at 3' ends) using the symmetric dimer CPG as the support in solid phase chemical synthesis using standard methods.

Figure 14A:
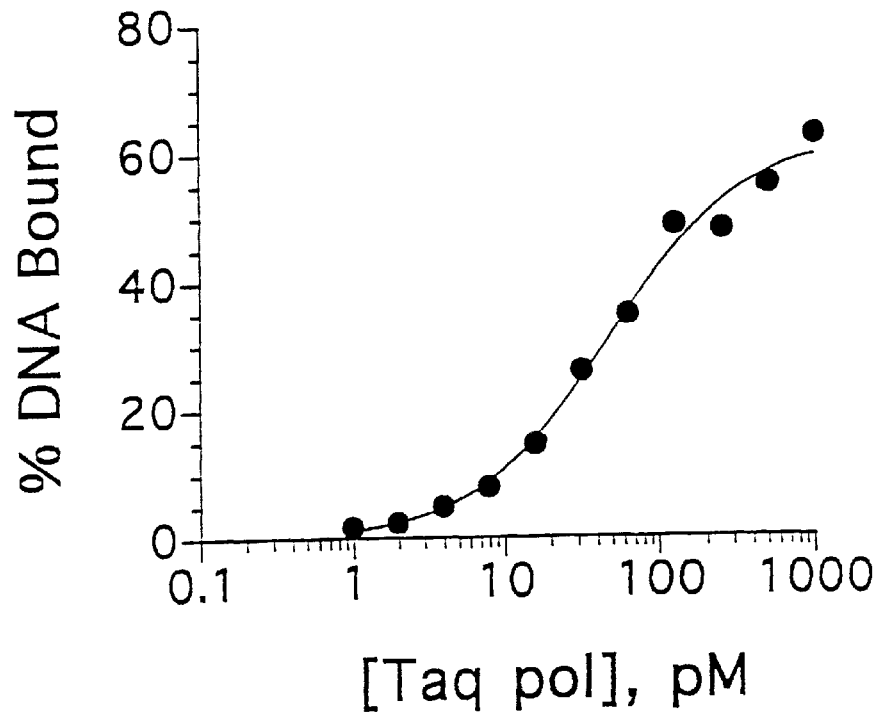
FIGS. 14A and 14B depict the affinity and inhibition characteristics of the homodimer (D.30-D.30) (SEQ ID NO:71).
Figure 14B:
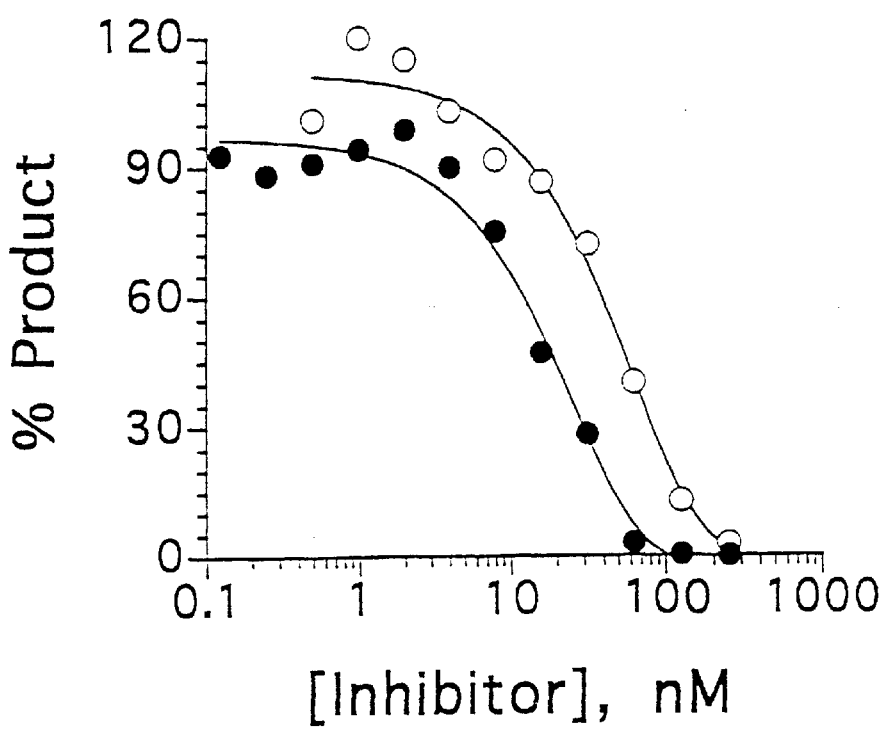

The affinity of D.30-D.30 dimer for binding to Taq polymerase is 40 pM (FIG. 14A), about 75-fold higher than its monomeric form. The $IC_{50}$ value of the homodimer is 14 nM, about 3.5-fold lower than the monomeric form (FIG. 14B). Thus, the dimerization of the truncated TQ30 produced a more effective inhibitor for Taq polymerase.

Two heterodimeric sequences in which the two monomeric truncates, Trnc.2-30 and Trnc-21 (Table 4), were joined by a linker containing 3 thymines were also prepared. In D.21-D.30 (SEQ ID NO:72) the Trnc-21 sequence is placed at the 5' end of the molecule, whereas in D.30-D.21 (SEQ ID NO:73) it occupies the 3' end of the molecule. Unlike the full-length TQ30, its truncated forms did not inhibit Tth polymerases. Trnc-2, on the other hand, inhibited both Taq and Tth polymerases, but not the Stoffel fragment. Assuming that the monomeric units are able to function independently, after being thethered into a single sequence, the combination of the two truncated ligands would provide a single sequence that could inhibit all three polymerases. At the lowest inhibitor concentration (62.5 nM) the inhibitory effect of the two heterodimers on Taq polymerase is higher than the two monomers. The effect of heterodimers on Tth polymerase is identical to that of the Trnc-21 monomer. The Stoffel fragment could not completely extend the hairpin template in the presence of the two heterodimers. In contrast, partially extended products were less abundant in the presence of the monomeric Trnc.2-30 sequence. The lack of the complete extension of the hairpin template suggests that the heterodimers do suppress the activity of the Stoffel fragment.

Figure 15A:
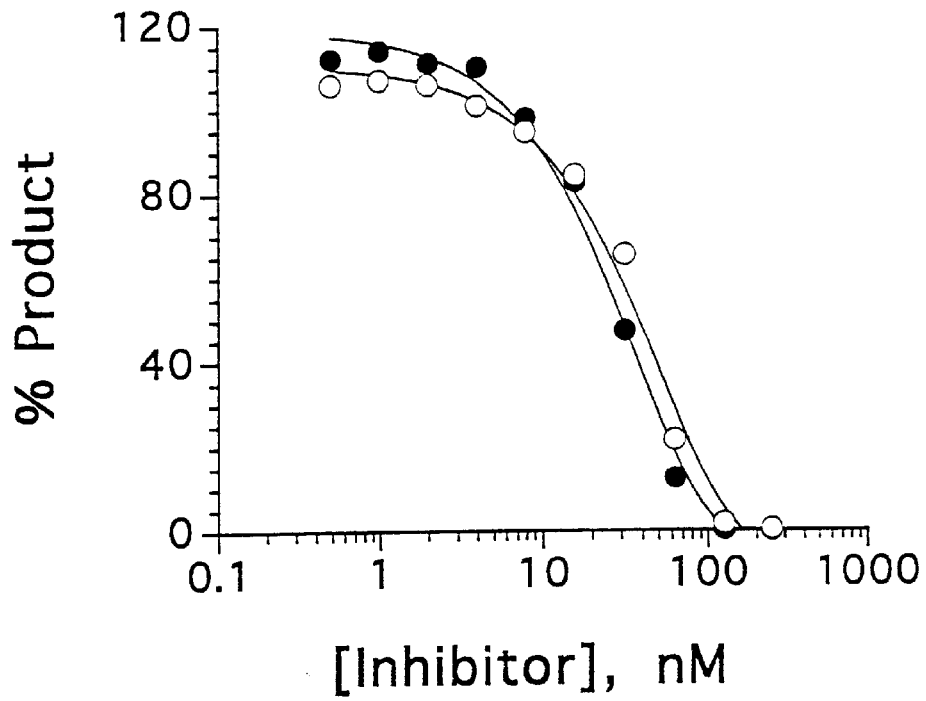
FIGS. 15A and 15B depict the inhibition characteristics of the heterodimer D.21-D.30 (SEQ ID NO:72).
Figure 15B:
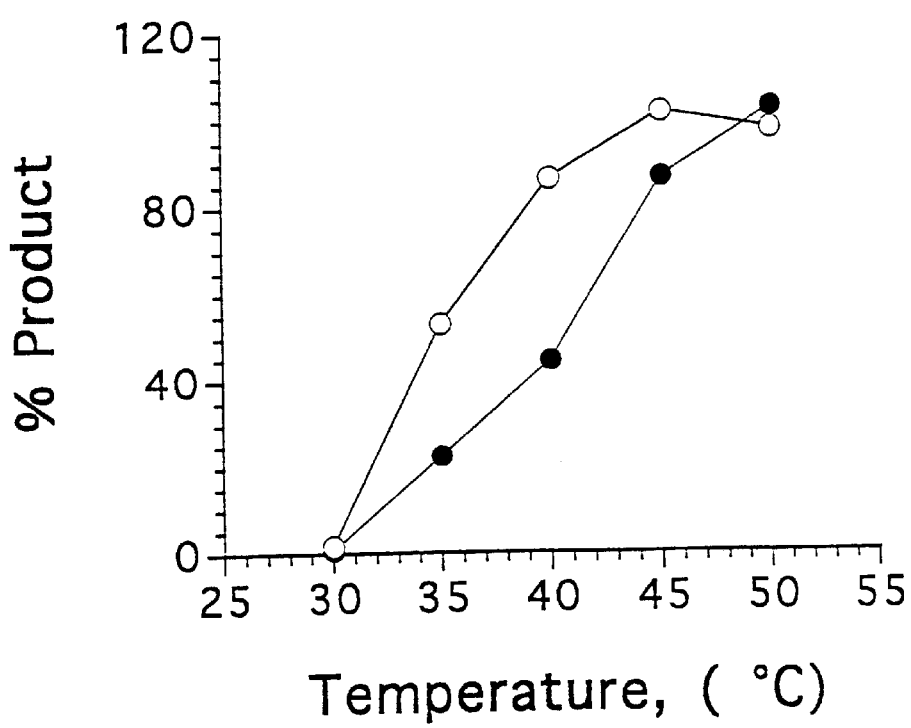
Figure 16A:
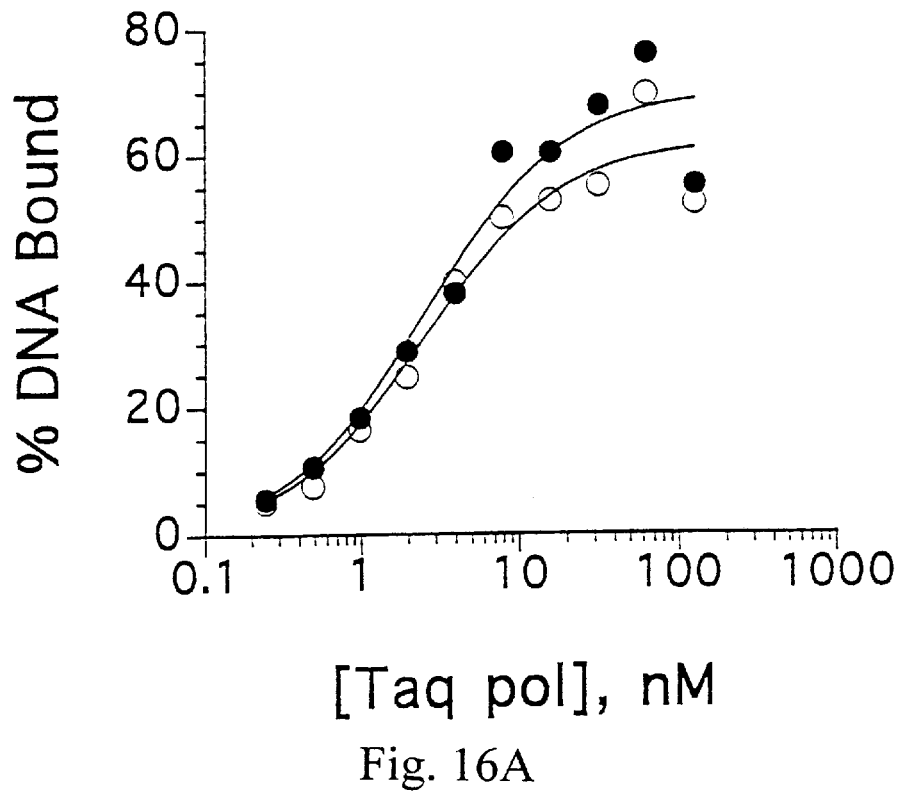
FIGS. 16A and 16B illustrate the effect of dNTPs and the hairpin template DNA on the binding affinity of Trnc.21 to Taq polymerase.
Figure 16B:
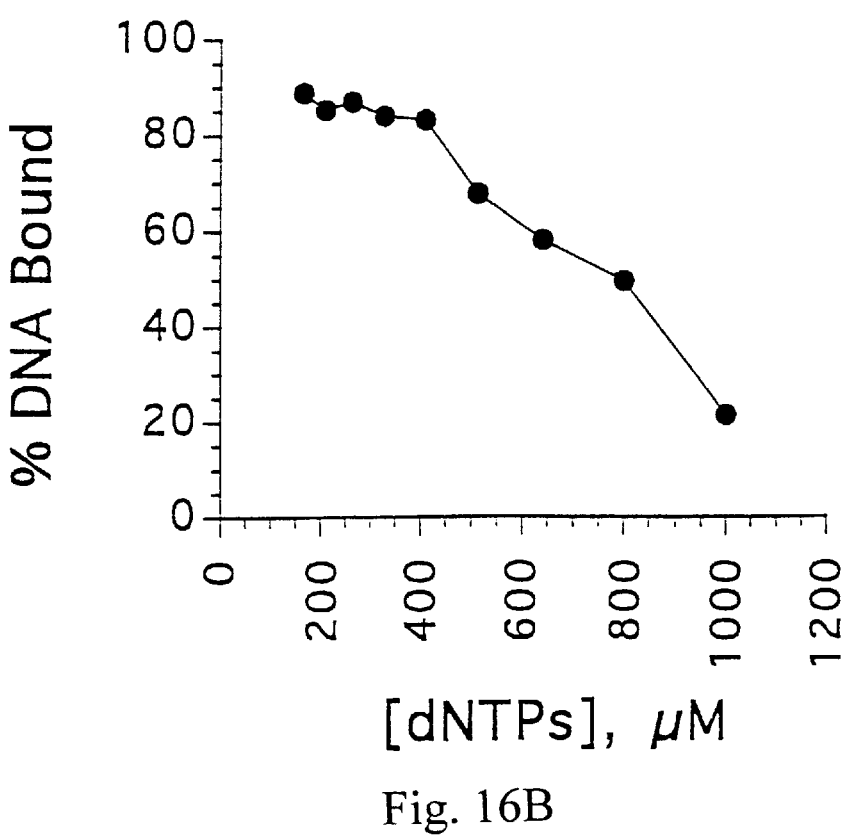

The heterodimer D.21-D.30 has an $IC_{50}$ value of approximately 30 nM for the inihibition of the Taq and Tth polymerases (FIG. 15A). The $IT_{50}$ values for the inhibition of the Taq and Tth polymerase are 41 and 34.5° C., respectively (FIG. 15B). D.21-D.30 inhibits the Stoffel fragment with an $IC_{50}$ value of 15.5 nM and an $IT_{50}$ value of 38° C. (data not shown). The $K_d$ of ligand D.21-D.30 heterodimer for binding to Taq polymerase is similar to that of the Trnc-21 (10 pM), suggesting that the protein preferentially binds to the sequence motif with high-affinity binding.

The positioning of the two monomeric units in the dimer seems to have no overall effect on the inhibition on any of the three polymerases. The two different monomeric units did not show adverse effect when they were combined into a dimer. As expected, the heterodimers showed the ability to inhibit all three polymerases quite effectively, indicating that by and large, functions of monomeric units in heterodimers are mutually exclusive.

The following Examples are provided to explain and illustrate the present invention and are not intended to be limiting of the invention.

EXAMPLE 1

Experimental Procedures

A. Materials and Methods.

Recombinant Taq polymerase (rTaq; Mr 94 kDa) suspended in a buffer consisting of 100 mM KCl, 20 mM Tris-HCl (pH 8.0), 0.1 mM EDTA, 50% glycerol (v/v) and 0.2% Tween 20 and recombinant Tth polymerase (rTth Mr 94 kDa) suspended in a buffer consisting of 50 mM Bicine-KOH (pH 8.3), 90 mM KCl and 50% glycerol (v/v) were purchased from Roche Molecular Systems, Inc. (Alameda, Calif.). Taq, Tth and UlTma DNA polymerases were obtained from Perkin Elmer. Ultma polymerase is a deleted form of Tma polymerase that lacks the wild type 5'→3' exonuclease activity. Tli and Tfl DNA polymerases were purchased from Promega. Tbr polymerase (Thermalase Thr) was obtained from Amresco Inc. Symmetrical branching 3'—3' linking CPG and C-6 Thiolmodifier phosphoramidites were obtained from Clontech (Palo Alto, Calif.). ULTRALINK™ Iodoacetyl beads were purchased from Pierce Chemicals (Rockford, Ill.). Enzymes used in radiolabeling of DNA were obtained from Boehringer Mannheim (Indianapolis, Ind.). All other reagents and chemicals were analytical grade and purchased from standard commercial sources.

Preparation of Oligonucleotides.

Oligonucleotides were synthesized by standard solid phase cyanoethyl phosphoramidite chemistry and purified by denaturing polyacrylamide gel electrophoresis to size homogeneity before use. The symmetrical homodimer was synthesized with Symmetrical Branching 3'—3' linking CPG. DNA concentrations were based on 33 µg/mL=1 $A_{260}$ Unit.

Preparation of Affinity Beads.

Twenty five nanomoles of either ligand TQ21 (SEQ ID NO:59) or TQ30 (SEQ ID NO:50) (Table 3) containing a thiol group at the 5' end was deprotected with $AgNO_3$ and dithiothreitol (DTT) according to Manufacturer's instructions. Excess DTT was removed by four sequential extractions with equal volumes of ethyl acetate. The deprotected ligand was then mixed with 500 µL of ULTRALINK™ iodoacetyl beads that had been washed two times in a buffer consisting of 50 mM Tris-HCl (pH 8.3) and 5 mM EDTA. The reaction mixture was incubated at room temperature for 2 hours on a rotating platform. Unreacted sites on the iodoacetyl beads were capped by reacting the mixture with 50 µL of a 0.5 M cysteine solution in the same buffer for 15 minutes. Control beads were prepared by reacting 500 µL of iodoacetyl beads with 500 µL of 0.5 M cysteine. After the reaction, the beads were washed five times with 500 µL of a PCR buffer consisting of 75 µM heparin, 12.5 mM $MgCl_2$, 50 mM KCl and 10 mM Tris-HCl (pH 8.3).

B. SELEX.

The SELEX procedure has been described in detail in U.S. Pat. No. 5,270,163. The SELEX experiments on both polymerases were performed using the template and primers shown in Table 1. The selection on Taq polymerase was carried out at room temperature in a buffer consisting of 10 mM Tris-HCl (pH 8.3; at 22° C.), 50 mM KCl and 2.5 mM $MgCl_2$ (Taq binding buffer). The selection on Tth polymerase was carried out in a buffer containing 50 mM Bicine-KOH (pH 8.3; at 25° C.), 90 mM KCl and 3.5 mM $Mn(OAc)_2$ (Tth binding buffer).

Each SELEX experiment was initiated with 5 nmoles of synthetic, gel-purified random sequence pool single stranded DNA (ssDNA) consisting of 30 nucleotide randomized region, flanked by 5' and 3' regions of fixed structure (Table 1). In a typical round of selection, ssDNA suspended in the appropriate binding buffer was heated to 90° C. for 3 minutes, chilled on ice, and then brought to room temperature. Once equilibrated at room temperature, the DNA was incubated for 15 minutes with the appropriate target polymerase in the presence of 2 nmoles of tRNA as a competitor and 0.01% human serum albumin (hSA). Polymerase-DNA complexes were separated from unbound DNA by nitrocellulose filtration through a prewet nitrocellulose filter (0.45 µM, Millipore) under suction. The filter was immediately washed with 20 mL of the binding buffer, 20 mL of 0.5 M urea in the binding buffer, and 0.5 M urea in water. Filter retained DNA was eluted and isolated by ethanol precipitation in the presence of carrier tRNA (5 µg).

The isolated DNA was amplified by PCR with Primer Set I (Table 1). One of the primer strands contained three contiguous biotins at the 5' end. The unbiotinylated strand of the resulting duplex DNA was isolated by gel electrophoresis under denaturing conditions (Pagratis et al. in preparation) and used for the next round of selection. In subsequent rounds, prior to incubating with the target polymerase, DNA pools were passed through nitrocellulose filters (counter selection) to remove DNA sequences that bind to the nitrocellulose filter. The number of picomoles of target polymerase was gradually decreased during the course of SELEX to increase the selective pressure for sequences with high affinity binding. The amount of DNA in each selection was kept at least five-fold higher than the amount of protein to ensure competition for high affinity binding DNA sequences.

The progress of SELEX was monitored by nitrocellulose filter binding analysis of enriched pools. The enriched pools that showed the highest affinity binding were PCR amplified with Primer Set II to incorporate BamHI and EcoRI restriction sites at the termini of the resulting duplex DNA. This DNA was gel purified and digested with BamHI and EcoRI and cloned into plasmid pUC18 vector previously digested with the same enzymes using standard techniques. (Sambrook et al. (1989) in *Molecular Cloning: A laboratory Manual*, 2nd ed., Part 3, pC.1, Cold Spring Harbor Laboratory Press, Cold Spring Harbor, N.Y.). Clones were isolated and sequenced by standard dideoxy sequencing technique (Sequenase kit from U.S. Biochemical, Cleveland, Ohio).

C. Nitrocellulose Filter Binding Assay

For isolation of DNA molecules that bind tightly to Taq polymerase and Tth polymerase, respectively, the nitrocellulose filter partitioning method was used as described in the SELEX Patent Applications. Briefly, gel-purified $^{32}P$ ss-DNA pools labeled at the 5' end were suspended in the binding buffer, heated to 80° C., chilled on ice and then brought to room temperature. The DNA (5–10 pM) was then incubated for 15 minutes at room temperature with varying amounts of the target polymerase in 50 µL of the appropriate binding buffer containing 0.1 µg of tRNA and 0.01% hSA. The DNA concentrations were kept lower than 100 pM to ensure equilibrium in the presence of excess protein concentrations. After 15 minutes the binding reaction mixtures were passed through pre-wet nitrocellulose/cellulose acetate mixed matrix filters (0.45 µm pore size, Millipore Corporation, Bedford, Mass.) and the filters were immediately washed with 5 mL of binding buffer. The amount of DNA bound to the filters was quantitated by measuring the radioactivity of the filters by liquid scintillation counting. The quantity of DNA bound to filters in the absence of protein was used for background correction. The percentage of input DNA retained on each filter was plotted against the corresponding log of the polymerase concentration (FIGS. 1 and 2). The nonlinear least square method was used to obtain the dissociation constants ($K_d$) of the DNA ligands to the Taq and Tth polymerases, respectively. (Schneider et al. (1995) Biochemistry 34:9599; Jellinek et al. (1993) Proc. Natl. Acad. Sci., U.S.A. 90:11227–11231).

Figure 1B:
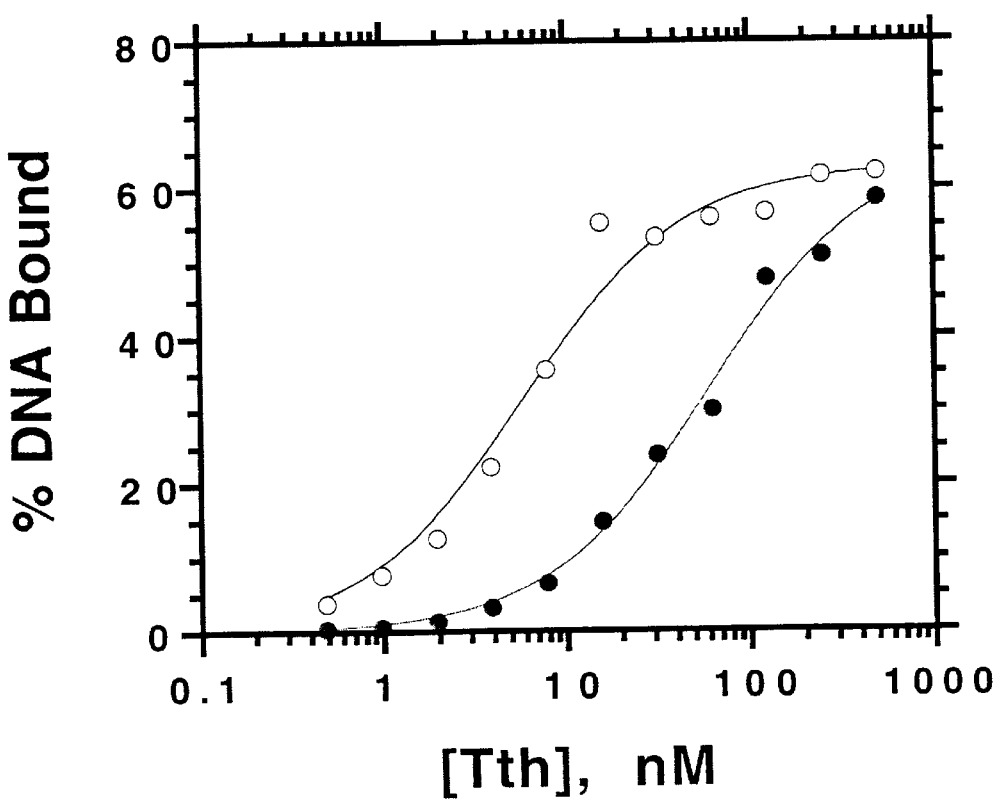
FIG. 1B shows the binding affinities of enriched pools of DNA after 10 rounds of SELEX (○) and the unselected random pool (●) of DNA for the Tth polymerase.

The unselected random sequence pool bind Tth polymerase with an estimated $K_d$ of approximately 70 nM (FIG. 1B, (●)), whereas the $K_d$ of this pool binding to Taq polymerase is approximately 50–100 nM (FIG. 1A, (○)). After 12 rounds of selection, the $K_d$ of binding to Taq polymerase was 3.5 nM (FIG. 1A, (○)). Additional rounds of selection did not result in further improvement of affinity. Thus, the resulting affinity of the enriched pool to Taq polymerase was significantly improved as compared to the unselected random pool. Similar results were obtained with the Tth polymerase where the pool from the 10th round showed a $K_d$ of 5 nM (FIG. 1B, (○)).

Figure 2A:
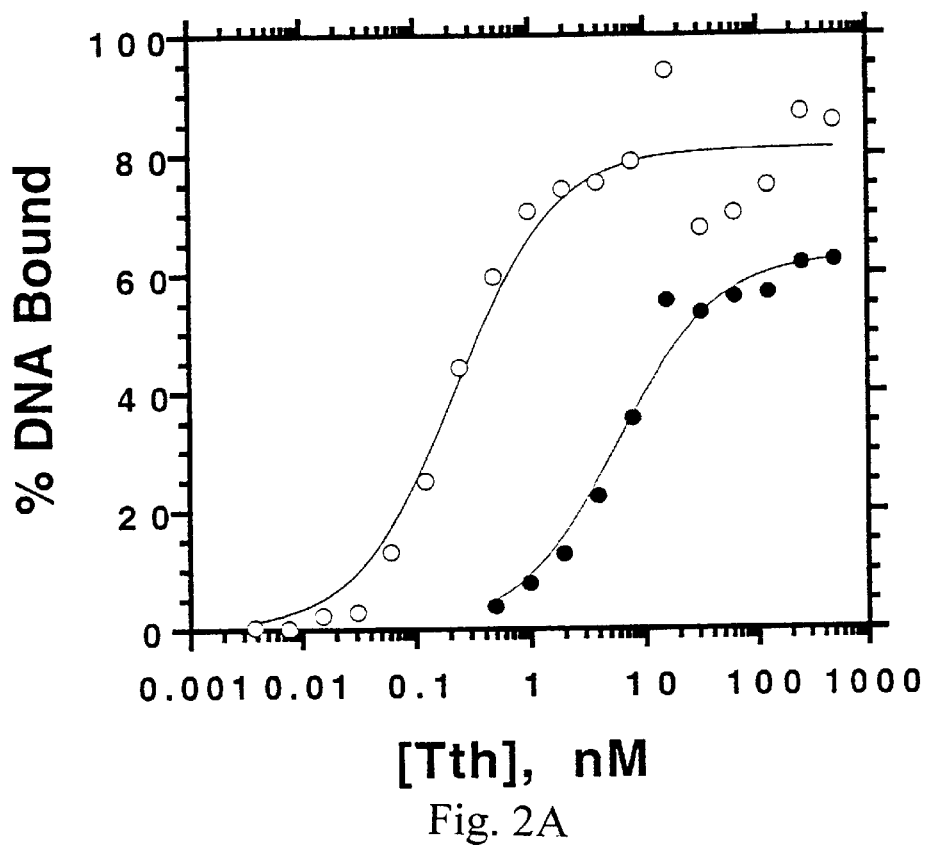
FIG. 2A shows a cross binding analysis of the enriched DNA pool for the Taq polymerase (○) and the enriched DNA pool for the Tth polymerase (●) to the Tth polymerase.
Figure 2B:
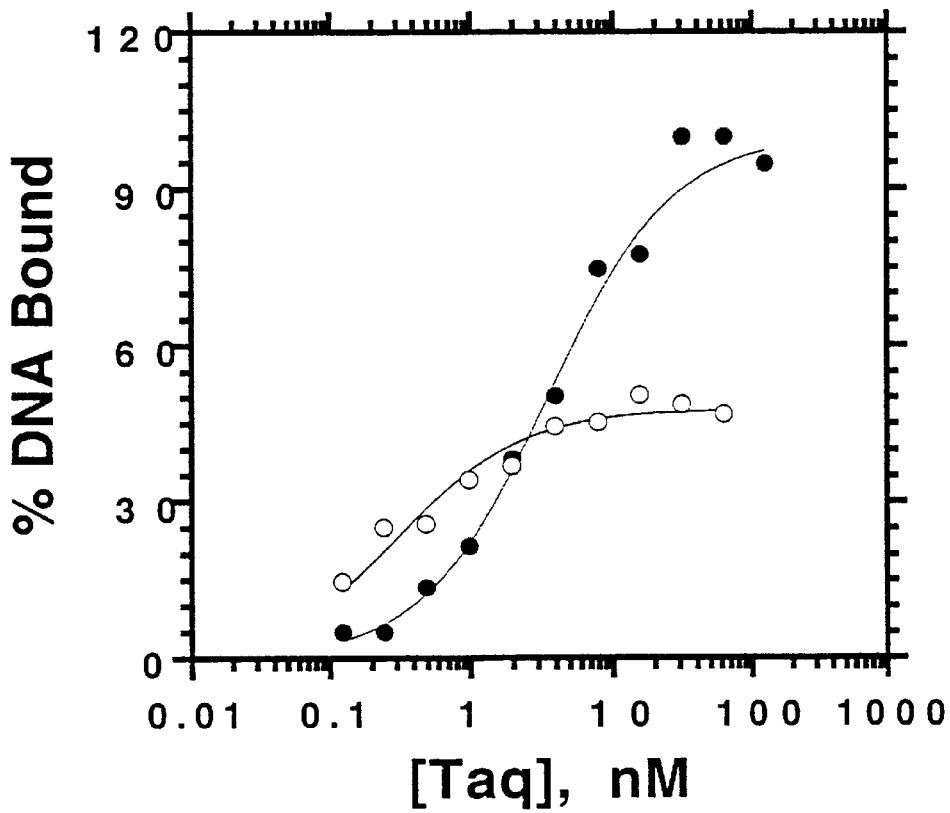
FIG. 2B shows a cross binding analysis of the enriched DNA pool for the Taq polymerase (○) and the enriched DNA pool for the Tth polymerase (●) to the Taq polymerase.

The ssDNA pool selected for Taq polymerase showed very tight binding to Tth polymerase with a $K_d$ of 0.2 nM (FIG. 2A, (○)). This result is not surprising, since the amino acid sequence identity between the two polymerases is approximately 87% (Asakura et al. (1993) J. Ferment. Bioeng. 76:265–269). The pool selected for Tth polymerase bound Taq polymerase in a different manner, with the binding saturating at around the 50% level (FIG. 2B, (○)), suggesting that about one half of the sequences in the pool are not interacting with Taq polymerase. Based on 50% saturation the estimated $K_d$ is 0.3 nM.

The ss-DNA sequences obtained from 10 rounds of selection performed with Tth polymerase are set forth in Table 2. Twenty nine individual clones were sequenced from the Tth polymerase selection (only the variable 30 nucleotide region is shown in Table 2). The sequences were grouped into two families based upon sequence similarity. The ss-DNA sequences obtained from 12 rounds of selection performed with Taq polymerase are set forth in Table 3. Thirty three unique sequences were isolated. The lowercase letters in some of the sequences depict the 5'-fixed sequence and the upper case letters depict the 30 nucleotide random region. The sequences were grouped into three families based on sequence similarity.

EXAMPLE 2

Polymerase Inhibition Assays

Figure 4:
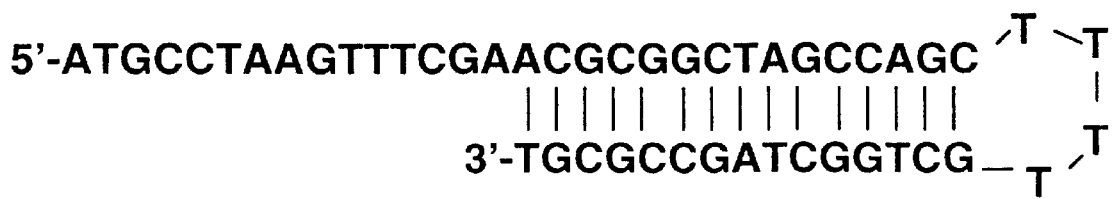
FIG. 4 illustrates DNA polymerization.
Figure 4:
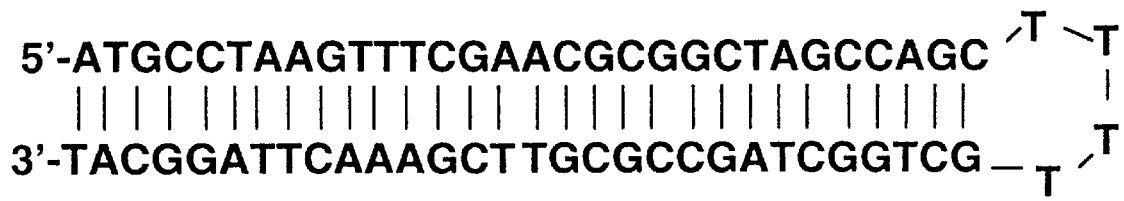

The polymerase inhibition assays were performed using the template DNA (DNA-HP; 5'-ATGCCTAAGTTTCGAACGCGGCTAG CCAGCTTTTGCTGGCTAGCCGCGT-3' (SEQ ID NO:6)), end-labeled at the 5' end with T4 polynucleotide kinase and $^{32}$P-γ-ATP and purified by gel electrophoresis under denaturing conditions (FIG. 4). In a representative experimental procedure, either 0.25 pmoles of Taq polymerase (5 U) or 0.125 pmoles (2.5 U) of Tth polymerase was mixed with 5 pmoles (250 nM) of the enriched pool, random pool or a specific DNA ligand in the standard PCR buffer (20 μL). Five pmoles (250 nM) of labeled template DNA-HP was added and the mixture was incubated at different temperatures for a given period of time. The reaction was stopped by adding EDTA to a final concentration of 125 mM (5 μL of 0.5 M EDTA). The DNA was resolved on a polyacrylamide gel under denaturing conditions. Gels were visualized by autoradiography and the percent DNA bound was quantitated by phosphoimager. Variations in this general procedure for specific reactions are noted in the Specification.

The order in which the oligonucleotide inhibitors are added to the reaction mixture is irrelevent, as long as, the template is added last. The oligonucleotides require $Mg^{++}$ ions, an essential component of PCR, to function and appear to tolerate many buffer systems.

FIG. 5 illustrates the results of the polymerase activity assays using the enriched pools of DNA. FIGS. 6–9 illustrate the results of the polymerase activity assays using ligands TQ30 (SEQ ID NO:50) and TQ21 (SEQ ID NO:59).

Measurement of $IC_{50}$ Values.

$IC_{50}$ values (the concentration of inhibitor required to produce 50% of the product in the assay) were obtained by using hairpin extension assay. In a typical inhibition assay, a 20 μL reaction contained either 0.25 pmoles of Taq polymerase (5 U) or 0.125 pmoles of Tth polymerase (2.5 U), oligonucleotide inhibitor (at varying concentrations), 10 mM Tris-HCl (pH 8.3), 50 mM KCl, 2.5 mM $MgCl_2$, and 1 mM each dNTPs. Gel purified, 5'-end-labeled hairpin DNA substrate (DNA-HP; 5'-ATGCCTAAGTTTCGAACGCGGCT AGCCAGCTTTTGCTGGCTAGCCGCGT-3') was then added to a final concentration of 250 nM and the reaction was incubated at 30° C. for 1 hour. The reaction was stopped by adding 5 μL of 0.5 M EDTA (pH 8.0) followed by formamide gel loading buffer. Extension products were resolved on 10% polyacrylamide gels under denaturing conditions. The amount of extension products were quantitated by phosphorimager. The amounts of products formed in the presence of inhibitor was normalized to the product formed in the absence of an inhibitor to obtain the percent of product.

Measurements of $IT_{50}$ Values.

Hairpin extension reactions were the same as descibed above, except that the inhibitor concentration was 250 nM. Incubation time at each temperature was 1 hour. The amount of product was quantitated by phosphorimager and normalized to the product formed in the absence of an inhibitor at the same temperature to obtain the percent of product.

Determination of Ligand TQ30 and Ligand TQ21 Substrate Activity.

In a representative experimental procedure 5'-end labeled ligand TQ30 (SEQ ID NO:50), TQ21 or TQ21 (3'-capped with an ethylene glycol linker) (approximately 3 pmole) was incubated in 20 μL of the binding buffer and 1 mM each dNTPs in the absence and presence of either 5 U of Taq polymerase or 2.5 U of Tth polymerase for 16 hours at room temperature. Capping of the 3'-end of TQ21 was accomplished with an ethylene glycol linker (3'-Spacer C3 support from Glen Research) using standard conditions known in the art.

Affinity Capture Assays.

The affinity capture reactions were performed at 70° C. for 5 minutes in a 100 μL reaction volume that contained: 75 μM heparin, 12.5 mM $MgCl_2$, 1 mM each dNTPs, 50 mM KCl, 10 mM Tris-HCl (pH 8.3), 5 U of Taq polymerase or 2.5 U of Tth polymerase and 250 nM 5'-end labeled hairpin assay template (DNA-HP). After 5 minutes the reaction mixture was diluted by three fold and cooled to 4° C. After round 1 synthesis, 15 μL of beads (either affinity beads or control beads, prepared as described above) were added to the reaction mixture at 4° C. and gently mixed for 10 minutes. Supernatants containing the labeled template were recovered after centrifugation and saved for gel analysis. The beads were then washed five times with 100 μL of a buffer consisting of 75 μM heparin, 12.5 mM $MgCl_2$, 50 mM KCl and 10 mM Tris-HCl (pH 8.3). After round 2 synthesis, the washed beads were mixed with a fresh aliquot of the reaction mixture containing all of the reagents except the polymerase. After incubating at 70° C. for 5 minutes, the reaction mixture was recovered and analyzed by gel electrophoresis.

EXAMPLE 3

Exonucleoase Inhibition Assay

The exonucleoase inhibition assays were performed using the designed template, 5'-TTCGAGCGTGAATCTGAATTCGCGGCTAGCCAG-CTTTTGCTG GCTAGCCGCGGTGGGAAACTGAGG-TAGGTAGGTGTTTTCACCTACCTCAG TTTCCCACC-3' (Exo-sub) (SEQ ID NO:75), radiolabeled at the 5' end (using [γ$^{32}$P]-ATP and T4 polynucleotide kinase) and at the 3' end using ([α$^{32}$P]-ddATP and deoxyterminaltransferase). In a representative experimental procedure either 5 U of Taq polymerase or 2.5 U of Tth polymerase was mixed with 250 nM of ligand TQ30 or ligand TQ21 in the standard PCR buffer (20 μL), followed by the addition of the double-labeled Exo-Sub (250 nM, added last). After incubating for 16 hours at room temperature, the reactions were quenched by addition of EDTA to 0.1 mM final concentration. Cleavage products were resolved on 8% polyacrylamide gels run under denaturing conditions.

EXAMPLE 4

Polymerase Inhibition Assays

Inhibition by TQ21 (SEQ ID NO:50) and TQ30 (SEQ ID NO:50) was tested on (A) thermophilic DNA polymerases, (B) mesophilic DNAPs (Taq polymerase as a control), and reverse transcriptases, and (C) RTs. All reactions were carried out in 20 μL volume with the HP hairpin template (Example 2) in the presence of 1 mM each dNTPs, using either 250 or 500 nM of ligand TQ21 or TQ30. Specific reaction conditions for each polymerase were as follows:

Thermostable polymerases: Tma polymerase: UlTma polmerase (6 U), 10 mM Tris-HCl, pH 8.8, 10 mM KCl, 2.5 mM $MgCl_2$ and 0.002% Tween 20 (v/v); Tbr polymerase (2 U), 10 mM Tris-HCl, pH 8.8, 50 mM KCl, 1.5 mM $MgCl_2$ and 0.01% Triton X-100; Tli polymerase (3 U) and Tfl polymerase (5 U), 10 mM Tris-HCl; pH 9.0, 50 mM KCl and 0.1% Triton X-100.

Mesophilic polymerases: All incubations including Taq polymerase (5 U) (an internal control for the buffer) were performed in a buffer consisting of 10 mM Tris-HCl, pH 7.5, 40 mM KCl, 5 mM $MgCl_2$ and 7.5 mM DTT (Klenow fragment (5 U); T4 DNA polymerase (4 U); T7 DNA polymerase (7 U)).

Reverse Transcriptases. All incubations were performed in a buffer consisting of 50 mM Tris-HCl, pH 8.3, 60 mM NaCl, 6 mM Mg(OAc)$_2$ and 10 mM DTT. (HIV-1 RT (0.56 pmoles); AMV RT (1 U); M-MLV RT (10 U); Superscript II (Ssript II) (10 U).

EXAMPLE 5

Detection of Low Copy Number Target

PCR amplifications were performed using a system that amplifies a 203-bp target-specific product from HIV-2 LTR as described by Respess et al. (1994) in *Interscience Conference on Antimicrobial Agents and Chemotherapy* 94:110). All PCR amplifications were carried out in the presence of 1.3 µg of human placental DNA, 0.4 mM each dNTP, 25 pmoles of each primer, 10 mM Tris-HCl (pH 8.3), 2.5 mM MgCl$_2$, 10% glycerol, 5 U of Taq polymerase and the template (approximate number of copies as indicated in FIGS. 10A–10C) in 100 µL reaction volume. Thermocycling was performed at 50° C. for 2 minutes followed by 94° C. for 30 sec; 60° C. for 30 seconds; 72° C. for 30 seconds and then autoextended 60° C. annealing in 1° C. increments for 5 cycles. This followed a 35-cycle amplification at 90° C. for 30 seconds; 65° C. for 30 seconds; 72° C. for 30 seconds.

"Hot start" PCR was performed by using "AmpliWax" beads (from Perkin Elmer) according to manufacture's instructions. All other PCR amplifications were carried out without "hot start" conditions.

"NeXstart" PCR was performed using ligands TQ30 and TQ21, (50 nM final concentration) as inhibitors. One amplification was performed in the presence of a nonspecific oligonucleotide (50 nM final concentration) for purposes of comparison.

TABLE 1

Starting Random Sequence Pool of ssDNA:

5'-TTCTCGGTTGGTCTCTGGCGGAGC-[N]$_{30}$-TCTTGTGTATGATTCGCTTTTCCC-3'　(SEQ ID NO:1)

SELEX PCR Primer Set I:

5'-TTCTCGGTTGGTCTCTGGCGGAGC-3'　(SEQ ID NO:2)

5'-BBBTAGGGAAAAGCGAATCATACACAAGA-3'　(SEQ ID NO:3)

(B represents Biotin)

SELEX PCR Primer Set II:

5'-GGC<u>GAATTC</u>TTCTCGGTTGGTCTCTGGCGGAGC-3'　(SEQ ID NO:4)
　　　EcoRI

5'-CGC<u>GGATCC</u>TAATACGACTCACTATAGGGAAAAGCGAATCATACACAAGA-3'　(SEQ ID NO:5)
　　　BamHI

TABLE 2

| SEQ ID NO: | CLONE NO: | SEQUENCE (5' → 3') |
|---|---|---|
| CLASS I | | |
| 7 | 2: | TATCGTTTACTCATT GTTTTG TGTGT |
| 8 | 34: | ACATTACCCGAGACATTCCTGAC GTTTTG |
| 9 | 21: | TGCTGCTCCTTGTTC GTTTTG TCT |
| 10 | 18: | AGCTTTTGGGGACATTCTAAC GTTTTG TCA |
| 11 | 19: | AGATGCTTCA GTTTTC TCTCCGTG |
| 12 | 16: | T CTTTTG GACTGAAGGTTTGTTGGT |
| 13 | 12: | ATGGTC TTTTTG TTGTTTGTTTG |
| 14 | 9: | GTGA CTTTTT ACTTGTCCTAGGCTG |
| 15 | 15: | CATCTAT GTCTTC TTTATATTTGG |
| 16 | 14: | ACTACCTGG TTGTGTG CTTTCCAT |
| 17 | 25: | ATCCATGAGACTAG GTTGGT TAGGGTGGTG |
| 18 | 1: | CCCTCATA GTTTAA CTTTACCTGGCTTATC |
| 19 | 10: | AGTGAACACCTTCT GTTTCG TGAGTC |
| 20 | 23: | CGTGT GTCTTA GTTAGCTCGTGG |
| 21 | 24: | TAACGTTGTGT GTTCTG TGCTA |
| 22 | 26: | AACAGATTTGGTCATAT TCCTTG G |
| 23 | 27: | TGTGTTAT GCTCCG GTAACAATGCCCTT |
| 24 | 30: | AATTGTA ATTTCG GTATCTCTG |
| 25 | 33: | GCA ATTTCC TGTCCAATCATTGTAG |
| 26 | 36: | GCTTGAA GCTTTC ACCCATCCTA/GA |
| 27 | 41: | CTTCTCCTTTATAT GTCTTA CCA |
| 28 | 42: | TATCGAGTAGACCCTGTT GTTCGT G |
| 29 | 44: | CGC GTCTAG CTAAGATTTCTACTGATGCAT |

TABLE 2-continued

| SEQ ID NO: | CLONE NO: | SEQUENCE (5' → 3') |
|---|---|---|
| 30 | 46: | ATG ATTTTA TGTTTATCCTGTTT |
| CLASS II | | |
| 31 | 45: | CAGTCGCTGTACGTGCTCTCCCTATGTAAC |
| 32 | 6: | CAATCGGTGTACAATATCTTC |
| 33 | 28: | CGTTAGCTGGTTAGTTAGTACTAG |
| 34 | 35: | AGGTAAGCGATTATGGGGTTATCG |
| 35 | 40: | TAGTTACATGAACTAATCGTGGAG |

TABLE 3

| SEQ ID NO: | CLONE NO: | | SEQUENCE (5'-3') | | |
|---|---|---|---|---|---|
| Family I | | | | | |
| 36 | 12: | (4) | ggcggagc | GATGTACAGTATC | GCTATCGAAAGAGGCTG |
| 37 | 15: | | ggcggagc | AGTGTGCAGTAGT | GTGATGTCAGAGTATCC |
| 38 | 18: | | ggcggagc | AGTGTGCGGTAGT | GTGATCTGAGAGTATCC |
| 39 | 26: | | ggcggagc | AGTGTGTAGTAGT | GTTACGATGGGACGG |
| 40 | 40: | | ggcggagc | AGTGTACAGTAGT | GTTCCCGGTAGAGCTAT |
| 41 | 27: | | ggcggagc | AATGTGCAGTATT | GATATCGCTGGTGGTCA |
| 42 | 10: | (2) | ggcggagcA | AGTGTACAGTAGT | TGCCTACGCTAGTG |
| 43 | 6: | | ggcggagcA | AGTGTACAGTAGT | TACTCATAAGAGACCA |
| 44 | 34: | | ggcggagcA | AGTGTACAGTAGT | TGCCTACGCTAGTG |
| 45 | 28: | | ggcggagcAC | AATGTGAAGTATT | GGGGTACGTCAGTAG |
| 46 | 5: | | CAAGCGGAAAC | AATGTACAGTATT | GGGATC |
| 47 | 33: | | AAGGCCATT | GATGTACAGTATC | AATGCTGC |
| 48 | 29: | | AATTGGGAAAC | AATGTGCAGTATG | TGAAGG |
| 49 | 44: | | AAATGGGAAAC | AATGTGCAGTATT | GGAAGG |
| 50 | 30: | (3) | AAGACCAGAC | AATGTACAGTATT | GGCCTGA |
| 76 | 3: | | TCAATACACAAATT | GATGTACAGTGTC | GAT |
| Family II | | | | | |
| 51 | 42: | | TACGCTGACAGGCC | ACGTTTTG | TCATGAT |
| 52 | 22: | | GAGAACTCCGTTCTTA | GCGTATTG | GAGTCC |
| 53 | 2: | | AGGTGGGACATTCTTT | GCGTTATG | TCTCTGA |
| 54 | 49: | | GGGCTCGGAACATTCTTA | GCGTTTTG | TTCC |
| 55 | 50: | | ATAGGCAGGGACATTGCA | ACCTTTTG | TCA |
| 56 | 7: | | AATTGAAGTGACTTTCTCT | GCGTTTAG | TCG |
| 57 | 39: | | AGGAATCTGGGCATTCTTT | GCGTTTTG | CG |
| 58 | 41: | | CTCAGGATAAGGTCATTCTA | ACGTTATG | A |
| 59 | 21: | | GATCATCTCAGAGCATTCTTA | GCGTTTTG | T |
| 60 | 31: | | GATCATCTAAGAGCATTCTTA | GCGTTTTG | G |
| 61 | 43: | | CAAAACGAGAGAGCTTTCTGT | GCGTTTAG | C |
| 62 | 23: | | GACCAAGCGTCAAGATATTCAA | ACGTTTTA | |
| 63 | 25: | | AGAAGCATACGAAGACATTCCA | ACGTTTGG | |
| 64 | 9: | (2) | AATCGATTGTTGAACATTCTG | ACGTTTTG | T |
| 65 | 17: | (2) | AGAAGCATACGAAGACATTCCA | ACGTTTTG | |
| 66 | 36: | | AGAAGCATACGAAGACATTCCA | ACGTTTTG | |

TABLE 3-continued

| SEQ ID NO: | CLONE: NO: | | SEQUENCE (5'-3') |
|---|---|---|---|
| | | Family III | |
| 77 | 4: | (2) | CATTGGGCCAGAGGAACACAACCTCAACAG |

10

TABLE 4

| SEQ ID NO: | CLONE NO: | SEQUENCE |
|---|---|---|
| 50 | TQ30 | 5'-ttctcggttggtctctggcggagcAAGACCAGACAATGTACAGTATTGGCCTGAtcttgtgtatgattcgctttccc-3' |
| 59 | TQ21 | 5'-ttctcggttggtctctggcggagcGATCATCTCAGAGCATTCTTAGCGTTTTGTtcttgtgtatgattcgctttccc-3' |
| 67 | Trnc. 1-30 | 5'-GGGACCAGACAATGTACAGTATTGTCTGGTCCC-3' |
| 68 | Trnc. 2-30 | 5'-GCCGGCCAATGTACAGTATTGGCCGGC-3' |
| 69 | Trnc. 3-30 | 5'-GGCCAATGTACAGTATTGGCC-3' |
| 70 | Trnc-21 | 5'-tggcggagcGATCATCTCAGAGCATTCTTAGCGTTTTGTtcttgtgtatga-3' |
| 71 | D.30-D.30 | 5'-GCCGGCCAATGTACAGTATTGGCCGGC ⎫<br>                                                          ⎬ X<br>5'-GCCGGCCAATGTACAGTATTGGCCGGC ⎭ |
| 72 | D.21-D.30 | 5'-tggcggagcGATCATCTCAGAGCATTCTTAGCGTTTTGTtcttgtgtatgaT<br>                                                                                                       T<br>3'-CGGCCGGTTATGACATGTAACCGGCCGT |
| 73 | D.30-D.21 | 5'-GCCGGCCAATGTACAGTATTGGCCGGCT<br>                                                                         T<br>3'-agtatgtgttctTGTTTTGCGATTCTTACGAGACTCTACTAGcgaggcggtT |

TABLE 5

| SEQ ID NO: | CLONE NO: | Secondary Structure[1] | $K^{2}_{d}$ (nM) | $T^{3}_{M}$ (° C.) |
|---|---|---|---|---|
| 74 | Trnc.A-30 (30-mer) | 5'-AAGAC      A_____A<br>         CAG  CAATGT     \<br>         \|\|\|  \|\|\|\|00   C ><br>         GTC  GTTATG     /<br>3'-A     CG_____A | 0.6 ± 0.1 | 51 |
| 67 | Trnc.1-30 (33-mer) | _____A<br>5'-GGGACCAGAGGCCAATGT     \<br>   \|\|\|\|\|\|\|\|\|\|\|\|\|\|\|\|00   C ><br>3'-CCCTGGTCCCGGTTATG     /<br>_____A | 2.0 ± 0.3 | 77 |
| 68 | Trnc.2-30 (27-mer) | _____A<br>5'-GCCGGCCAATGT     \<br>   \|\|\|\|\|\|\|\|\|\|\|\|00   C ><br>3'-CGGCCGGTTATG     /<br>_____A | 3.1 ± 0.3 | 81.5 |
| 69 | Trnc.3-30 (24-mer) | A<br>5'-GGCCAATGT<br>   \|\|\|\|\|\|\|\|\|00   C<br>3'-CCGGTTATG<br>A | 2.8 ± 0.4 | 65.5 |

TABLE 5-continued

| SEQ ID NO: | CLONE NO: | Secondary Structure[1] | $K^2_d$(nM) | $T^3_M$(° C.) |
| --- | --- | --- | --- | --- |

[1]The boxed region denotes the conserved sequence element with the predicted stem-loop structure identified in the Family I sequences; vertical lines signify Watson-Crick type base pairing; circles show an uncommon G-T base pair.
[2]$K_d$ values were measured by the nitrocellulose filter binding technique described in Example 1.
[3]Melting transitions ($T_m$) were measured in a PCR buffer containing 10 mM Tris-HCl, 50 mM KCl, 2 mM $MgCl_2$, pH 8.3, at a 1° C./min temperature ramp.

We claim:

1. A method for inhibiting the activity of a thermostable DNA polymerase, comprising adding a nucleic acid ligand that inhibits said DNA polymerase to a DNA polymerization reaction which is being maintained at a temperature at or below which said ligand inhibits polymerization.

2. The method of claim 1 wherein said DNA polymerase nucleic acid ligand is identified according to the method comprising:
   a) preparing a candidate mixture of nucleic acids;
   b) contacting the candidate mixture of nucleic acids with said polymerase, wherein nucleic acids having an increased affinity to the polymerase relative to the candidate mixture may be partitioned from the remainder of the candidate mixture;
   c) partitioning the increased affinity nucleic acids from the remainder of the candidate mixture; and
   d) amplifying the increased affinity nucleic acids to yield a mixture of nucleic acids enriched for nucleic acid sequences with relatively higher affinity and specificity for binding to the polymerase, whereby nucleic acid ligands of the polymerase may be identified.

3. The method of claim 1 wherein said DNA polymerase is Taq polymerase.

4. The method of claim 3 wherein said polymerase ligand is a DNA selected from one of the ligands of Table 2 (SEQ ID NOS:7–35), Table 3 (SEQ ID NOS:36–66, 76, 77), Table 4 (SEQ ID NOS:67–73) or Table 5 (SEQ ID NO:74).

5. The method of claim 1 wherein said DNA polymerase is Tth polymerase.

6. The method of claim 5 wherein said polymerase ligand is a DNA selected from one of the ligands of Table 2 (SEQ ID NOS:7–35), Table 3 (SEQ ID NOS:36–66, 76, 77), Table 4 (SEQ ID NOS:67–73) or Table 5 (SEQ ID NO:74).

7. A purified and isolated non-naturally occurring nucleic acid ligand to a thermostable polymerase.

8. The nucleic acid ligand of claim 7 identified according to the method comprising:

a) preparing a candidate mixture of nucleic acids;

b) contacting the candidate mixture of nucleic acids with said polymerase, wherein nucleic acids having an increased affinity to the polymerase relative to the candidate mixture may be partitioned from the remainder of the candidate mixture;

c) partitioning the increased affinity nucleic acids from the remainder of the candidate mixture; and d) amplifying the increased affinity nucleic acids to yield a mixture of nucleic acids enriched for nucleic acid sequences with relatively higher affinity and specificity for binding to the polymerase, whereby nucleic acid ligands of the polymerase may be identified.

9. The purified and isolated non-naturally occurring nucleic acid ligand of claim 7, wherein said polymerase is Taq polymerase and wherein said ligand is selected from the group consisting of the sequences set forth in Table 2 (SEQ ID NOS:7–35), Table 3 (SEQ ID NOS:36–66, 76, 77), Table 4 (SEQ ID NOS:67–73) and Table 5 (SEQ ID NO:74).

10. The purified and isolated non-naturally occurring nucleic acid ligand of claim 7, wherein said polymerase is Tth polymerase, and wherein said nucleic acid ligand is selected from the group consisting of the sequences set forth in Table 2 (SEQ ID NOS:7–35), Table 3 (SEQ ID NOS:36–66, 76, 77), Table 4 (SEQ ID NOS:67–73) and Table 5 (SEQ ID NO:74).

11. A purified and isolated non-naturally occurring nucleic acid ligand to a thermostable reverse transcriptase.

12. The nucleic acid ligand to the reverse transcriptase of claim 11 identified according to the method comprising:

a) preparing a candidate mixture of nucleic acids;

b) contacting the candidate mixture of nucleic acids with the reverse transcriptase, wherein nucleic acids having an increased affinity to the reverse transcriptase relative to the candidate mixture may be partitioned from the remainder of the candidate mixture;

c) partitioning the increased affinity nucleic acids from the remainder of the candidate mixture; and d) amplifing the increased affinity nucleic acids to yield a mixture of nucleic acids enriched for nucleic acid sequences with relatively higher affinity and specificity for binding to the reverse transcriptase, whereby nucleic acid ligands of the reverse transcriptase may be identified.

13. The purified and isolated non-naturally occurring nucleic acid ligand of claim 11, wherein said reverse transcriptase is Tth polymerase, and wherein said nucleic acid ligand is selected from the group consisting of the sequences set forth in Table 2 (SEQ ID NOS:7–35), Table 3 (SEQ ID NOS:36–66, 76, 77), Table 4 (SEQ ID NOS:67–73) and Table 5 (SEQ ID NO:74).

14. A method for performing the Polymerase Chain Reaction (PCR) comprising:

a) mixing a sample containing a nucleic acid sequence that is to be amplified with primers that are complementary to the sequences that flank the sequence to be amplified, Taq polymerase, and a nucleic acid ligand that inhibits the polymerase at a temperature at or below which said ligand inhibits polymerization, yet allows the polymerase to be activated at elevated temperatures; wherein said nucleic acid ligand is selected from the group consisting of the sequences set forth in Table 2 (SEQ ID NOS:7–35), Table 3 (SEQ ID NOS:36–66, 76, 77), Table 4 (SEQ ID NOS:67–73) and Table 5 (SEQ ID NO:74); and b) performing the standard PCR steps of melting the target nucleic acid, annealing the primers to the target nucleic acid, and synthesizing the target nucleic acid by thermal cycling of the mixture.

15. A method for performing the Polymerase Chain Reaction (PCR) comprising:

a) mixing a sample containing a nucleic acid sequence that is to be amplified with primers that are complementary to the sequences that flank the sequence to be amplified, Tth polymerase, and a nucleic acid ligand that inhibits the polymerase at a temperature at or below which said ligand inhibits polymerization, yet allows the polymerase to be activated at elevated temperatures; wherein said nucleic acid ligand is selected from the group consisting of the sequences set forth in Table 2 (SEQ ID NOS:7–35), Table 3 (SEQ ID NOS:36–66, 76, 77), Table 4 (SEQ ID NOS:67–73) and Table 5 (SEQ ID NO:74); and b) performing the standard PCR steps of melting the target nucleic acid, annealing the primers to the target nucleic acid, and synthesizing the target nucleic acid by thermal cycling of the mixture.

16. A PCR kit comprising a thermostable DNA polymerase and a nucleic acid ligand that inhibits said polymerase at a temperature below which said ligand inhibits polymerization, yet allows the polymerase to be activated at elevated temperatures, wherein said thermostable DNA polymerase is Taq polymerase and wherein said nucleic acid ligand is selected from the group consisting of the sequences set forth in Table 2 (SEQ ID NOS:7–35), Table 3 (SEQ ID NOS:36–66, 76, 77), Table 4 (SEQ ID NOS:67–73) and Table 5 (SEQ ID NO:74).

17. A PCR kit comprising a thermostable DNA polymerase and a nucleic acid ligand that inhibits said polymerase at a temperature below which said ligand inhibits polymerization, yet allows the polymerase to be activated at elevated temperatures, wherein said thermostable DNA polymerase is Tth polymerase and wherein said nucleic acid ligand is selected from the group consisting of the sequences set forth in Table 2 (SEQ ID NOS:7–35), Table 3 (SEQ ID NOS:36–66, 76, 77), Table 4 (SEQ ID NOS:67–73) and Table 5 (SEQ ID NO:74).

* * * * *